United States Patent
Osborn, III et al.

[11] Patent Number: 5,891,126
[45] Date of Patent: *Apr. 6, 1999

[54] ABSORBENT INTERLABIAL DEVICE TREATED WITH A POLYSILOXANE EMOLLIENT

[75] Inventors: Thomas Ward Osborn, III; Thomas James Klofta, both of Cincinnati, Ohio

[73] Assignee: The Procter & Gamble Company, Cincinnati, Ohio

[*] Notice: The term of this patent shall not extend beyond the expiration date of Pat. No. 5,643,588.

[21] Appl. No.: 869,700

[22] Filed: Jun. 5, 1997

Related U.S. Application Data

[63] Continuation-in-part of Ser. No. 706,371, Aug. 28, 1996, Ser. No. 778,521, Jan. 3, 1997, Ser. No. 778,925, Jan. 3, 1997, and Ser. No. 778,520, Jan. 3, 1997.

[51] Int. Cl.⁶ .................................................. A61F 13/15
[52] U.S. Cl. ...................... 604/385.1; 604/363; 604/904
[58] Field of Search ..................... 424/402; 604/385.1, 604/363, 904

[56] References Cited

U.S. PATENT DOCUMENTS

| | | |
|---|---|---|
| 2,092,346 | 9/1937 | Arone . |
| 2,662,527 | 12/1953 | Jacks . |
| 2,917,049 | 12/1959 | Delaney . |
| 3,420,235 | 1/1969 | Harmon . |
| 3,905,372 | 9/1975 | Denkinger . |
| 3,983,873 | 10/1976 | Hirschman . |
| 4,175,561 | 11/1979 | Hirschman . |
| 4,412,833 | 11/1983 | Weigner et al. . |
| 4,413,986 | 11/1983 | Jacobs . |
| 4,595,392 | 6/1986 | Johnson et al. . |
| 4,631,062 | 12/1986 | Lassen et al. . |
| 4,846,824 | 7/1989 | Lassen et al. . |
| 5,484,429 | 1/1996 | Vukos et al. . |
| 5,635,191 | 6/1997 | Roe et al. . |
| 5,643,588 | 7/1997 | Roe et al. ................................ 424/402 |
| 5,762,644 | 6/1998 | Osborn, III et al. ................. 604/385.1 |

FOREIGN PATENT DOCUMENTS

| | | | |
|---|---|---|---|
| 0 685 215 A1 | 12/1995 | European Pat. Off. | ........ A61F 13/20 |
| 0 692 263 A2 | 1/1996 | European Pat. Off. | ........ A61L 15/50 |

*Primary Examiner*—Robert A. Clarke
*Assistant Examiner*—Miley Craig Peppers, III
*Attorney, Agent, or Firm*—Bart S. Hersko; Edward J. Milbrada; Jeffrey V. Bamber

[57] ABSTRACT

Absorbent devices, and more particularly absorbent devices that are worn interlabially by female wearers for catamenial purposes, incontinence protection, or both, that have a emollient composition on their body-contacting surface are disclosed. The interlabial device has a body-contacting surface that is pre-moistened or pre-treated with an emollient to prevent drying of the wearer's labial tissue and to reduce friction of the structure against the wearer's labial tissue. The absorbent device is preferably capable of maintaining contact with the inside surfaces of the wearer's labia majora when worn. The emollient composition comprises a plastic or fluid emollient such as mineral oil, petrolatum and/or polysiloxane, an immobilizing agent such as a fatty alcohol or wax to immobilize the emollient on the body-contacting surface of the device, and optionally a hydrophilic surfactant to improve wettability of the coated surface. Because the emollient is substantially immobilized on the surface of the absorbent device, less emollient is required to impart the desired therapeutic or protective emollient coating benefits.

32 Claims, 6 Drawing Sheets

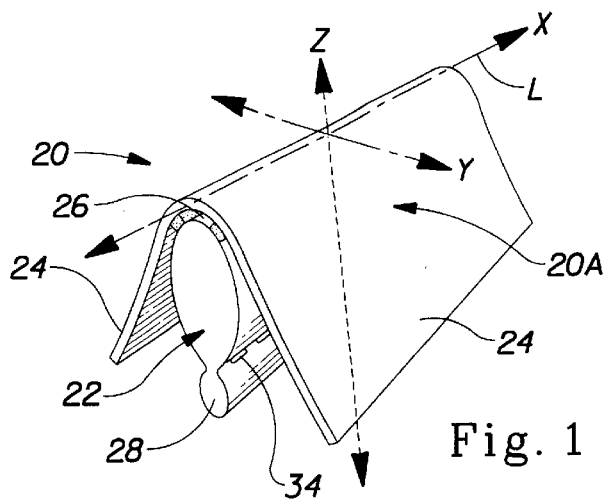
Fig. 1
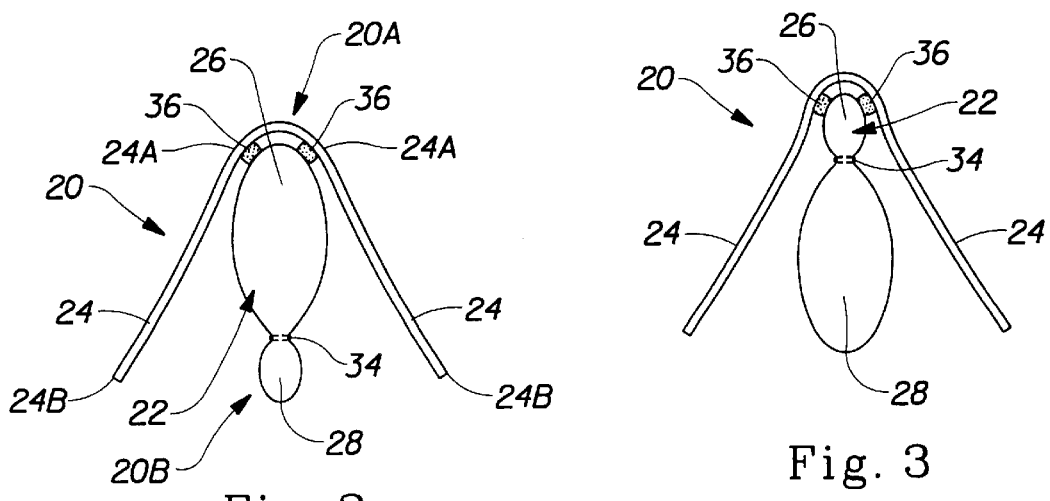
Fig. 2
Fig. 3
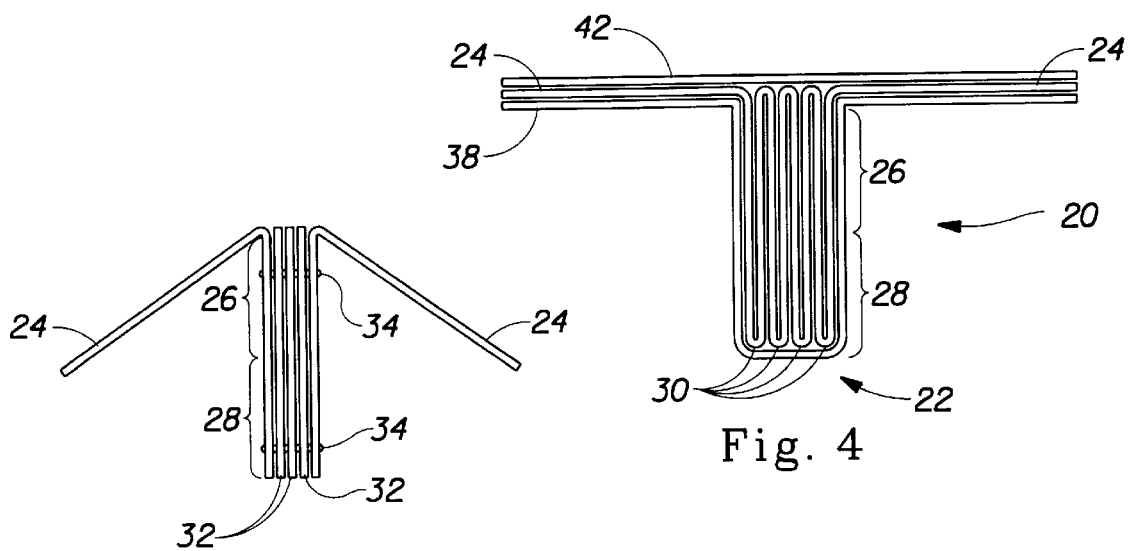
Fig. 4
Fig. 5

ABSORBENT INTERLABIAL DEVICE TREATED WITH A POLYSILOXANE EMOLLIENT

This application is a Continuation-In-Part of U.S. patent application Ser. No. 08/706,371, filed on Aug. 28, 1996; and a Continuation-In-Part of U.S. patent application Ser. No. 08/778,521, filed on January 1997; and a Continuation-In-Part of U.S. patent application Ser. No. 08/778,925, filed on Jan. 28, 1997; and a Continuation-In-Part of U.S. patent application Ser. No. 08/778,520, filed on Jan. 3, 1997.

FIELD OF THE INVENTION

The present invention relates to an absorbent device that is worn interlabially for catamenial purposes, incontinence protection, or both. More particularly, the present invention relates to an interlabial device that is pre-moistened or pre-treated with an emollient for improved comfort.

BACKGROUND OF THE INVENTION

All manner and variety of absorbent articles configured for the absorption of body fluids such as menses, urine and feces are, of course, well known. With respect to feminine protection devices, the art has offered two basic types; sanitary napkins have been developed for external wear about the pudendal region while tampons have been developed for internal wear within the vaginal cavity for interruption of menstrual flow therefrom. Such tampon devices are disclosed in U.S. Pat. No. 4,412,833, entitled "Tampon Applicator", issued to Weigner, et al. on Nov. 1, 1983, and U.S. Pat. No. 4,413,986, entitled "Tampon Assembly With Means For Sterile Insertion", issued to Jacobs on Nov. 8, 1983.

Hybrid devices which attempt to merge the structural features of the sanitary napkins and the tampons into a single device have also been proposed. Such hybrid devices are disclosed in U.S. Pat. No. 2,092,346, entitled "Catamenial Pad", issued to Arone on Sep. 7, 1937, and U.S. Pat. No. 3,905,372, entitled "Feminine Hygiene Protective Shield", issued to Denkinger on Sep. 16, 1975. Other less intrusive hybrid devices are known as labial or interlabial sanitary napkins and are characterized by having a portion which at least partially resides within the wearer's vestibule and a portion which at least partially resides external of the wearer's vestibule. Such devices are disclosed in U.S. Pat. No. 2,662,527, entitled "Sanitary Pad", issued to Jacks on Dec. 15, 1953, and U.S. Pat. No. 4,631,062, entitled "Labial Sanitary Pad", issued to Lassen, et al. on Dec. 23, 1986.

Interlabial pads have the potential to provide even greater freedom from inconvenience because of their small size and reduced risk of leakage. Numerous attempts have been made in the past to produce an interlabial pad which would combine the best features of tampons and sanitary napkins while avoiding at least some of the disadvantages associated with each of these types of devices. Examples of such devices are described in U.S. Pat. No. 2,917,049 issued to Delaney on Dec. 15, 1959, U.S. Pat. No. 3,420,235 issued to Harmon on Jan. 7, 1969, U.S. Pat. No. 4,595,392 issued to Johnson, et al. on Jun. 17, 1986, and U.S. Pat. No. 5,484,429 issued to Vukos, et al. on Jan. 16, 1996. A commercially available interlabial device is FRESH 'N FIT® PADETTE interlabial product which is marketed by Athena Medical Corp. of Portland, Oreg. and described in U.S. Pat. Nos. 3,983,873 and 4,175,561 issued to Hirschman on Oct. 5, 1976 and Nov. 27, 1979, respectively.

However, many of these devices have not met with great commercial success. There are drawbacks associated with all of the above products. The devices described in these patents are believed to potentially be uncomfortable to wear due to frictional discomfort associated with rubbing of the product against the labial walls and sticking of the surfaces of the device to the labial walls. Furthermore, the frictional drag and sticking of the body-contacting surface of such devices against the labia can prevent these devices from being properly inserted, leading to discomfort.

The problem of drying of a female wearer's labial vestibule area has been discussed in the patent literature. For example, U.S. Pat. No. 4,846,824 issued to Lassen, et al. on Jul. 11, 1989, is directed to a labial sanitary pad that has a "physiologically hydrous" cover (that is, a cover material supposedly designed to "maintain a moist interface between the tissues of the vestibule and the pad"). Types of cover materials specified in the Lassen, et al. patent include a spunlaced polyester fiber nonwoven and a rayon cover. The Lassen, et al. patent states that the covers can be provided with various "coatings" to maintain the physiologically hydrous feature, but no specific coatings appear to be disclosed.

European Patent Application EP 0 692 263 A2, "Method of reducing the coefficient of friction of absorbent products and wax coated products produced thereby", is directed to lubricated absorbent products having a coating of a small amount of high molecular weight solid waxy substance which has a softening point above body temperature. However, there are drawbacks associated with the use of high molecular weight materials for this purpose. High molecular weight materials will not be as soothing or lotion-like to the wearer's skin as lower molecular weight materials. In addition, high molecular weight materials will not be capable of transferring to the wearer's skin to provide skin care benefits. High molecular weight waxes can also become brittle and tend to flake or chip off an absorbent article due to their lack of flexibility if the absorbent article is of a type that is required to flex and bend. Further, if the softening point of such materials is higher than room temperature, application of such materials to an absorbent article will be more difficult, and will require that the material be heated in order to coat an absorbent article with such a material.

A vaginal moisture balanced tampon and process is disclosed in European Patent Application 0 685 215 A1. However, the interlabial device of the present invention is not intended to be worn inter-vaginally as a tampon.

Thus, a need exists for an interlabial device that is small in size and that can be easily inserted and that provides protection against incontinence, menstrual discharges, and discharges of bodily exudates throughout a great range of wearer motions. A need exists for an interlabial device which is absorbent, has a reduction in frictional discomfort associated with rubbing of the product against the labial walls and sticking of the surfaces of the device to the labial walls. A need also exists for an interlabial device that has a reduced tendency to dry the inside surface of the wearer's labia.

Therefore, it is an object of the present invention to provide an interlabial device that is small in size and that can be easily inserted and that provides protection against incontinence, menstrual discharges, and discharges of bodily exudates throughout a great range of wearer motions.

It is another object of the present invention to provide an interlabial device which is absorbent, but has a reduction in frictional discomfort associated with rubbing of the product against the labial walls and sticking of the surfaces of the device to the labial walls.

It is another object of the present invention to provide an interlabial device that has a reduced tendency to dry the inside surface of the wearer's labia.

It is still another object of the present invention to provide an interlabial lo device that can be inserted into the space between the wearer's labia with less friction so that it will more easily be fully inserted into the desired wearing position.

These and other objects of the present invention will become more readily apparent when considered in reference to the following description and when taken in conjunction with the accompanying drawings.

SUMMARY OF THE INVENTION

This invention relates to absorbent devices, and more particularly to an absorbent device that is insertable into the interlabial space of a female wearer for catamenial purposes, incontinence protection, or both. The interlabial device has a body-contacting surface (in particular, a surface contacting the labial vestibule) which is pre-treated with an emollient to prevent drying of the wearer's labial tissue and to reduce friction of the structure against the wearer's labial tissue.

The absorbent interlabial device of the present invention, in one preferred embodiment, comprises a main absorbent portion and a pair of flexible extensions joined to the main absorbent portion. The main absorbent portion preferably comprises an upper portion and a lower portion opposed to the lower portion. The upper portion faces toward the vestibule floor of the wearer during insertion of the absorbent device into the wearer's interlabial space and during use. That is, the upper portion is positioned furthest inward into the space between the wearer's labia thus leading the lower portion of the absorbent device during insertion. Upon insertion, the lower portion is less fully inserted into the wearer's interlabial space than the upper portion and the lower portion faces away from the floor of the vestibule of the wearer. The flexible extensions preferably extend downwardly and outwardly from the upper portion of the main absorbent portion and are joined to the same. The flexible extensions are preferably capable of maintaining contact with inside surfaces of the wearer's labia and covering a substantial portion of the same.

At least a portion of said body-contacting surface of the interlabial device comprises an effective amount of an emollient coating which is preferably semisolid or solid at ambient temperature, 68° F. (or 20° C). The coating preferably comprises a substantially water-free emollient having a plastic or fluid consistency at 20° C. and comprising a member selected from the group consisting of petroleum-based emollients, fatty acid ester emollients, alkyl ethoxylate emollients and/or polysiloxane emollients, and mixtures thereof In a preferred embodiment, the emollient contains about 5% or less water and comprises a petroleum based emollient selected from the group consisting of mineral oil, petrolatum, and mixtures thereof. In an alternate preferred embodiment, the emollient emollient contains about 5% or less water and comprises a polysiloxane emollient.

The emollient-treated interlabial device provides a reduction in frictional discomfort associated with rubbing of the product against the labial walls and sticking of the surfaces of the device to the labial walls. The emollient-treated interlabial device also has a reduced tendency to dry the inside surface of the wearer's labia. The interlabial device, because of the presence of the emollient, can be inserted into the space between the wearer's labia with less friction so that it will more easily be fully inserted into the desired wearing position.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

FIG. 1 is a perspective view of a preferred embodiment of the absorbent interlabial device of the present invention.

FIG. 2 is an end view of the absorbent device shown in FIG. 1.

FIG. 3 is an end view of a variation of the preferred embodiment shown in FIG. 2.

FIG. 4 is an end view of an alternative preferred embodiment of the present invention having a pleated main absorbent portion.

FIG. 5 is an end view of an alternative preferred embodiment of the present invention showing a main absorbent portion having a multiple layer structure.

DETAILED DESCRIPTION OF THE INVENTION

Figure 6:
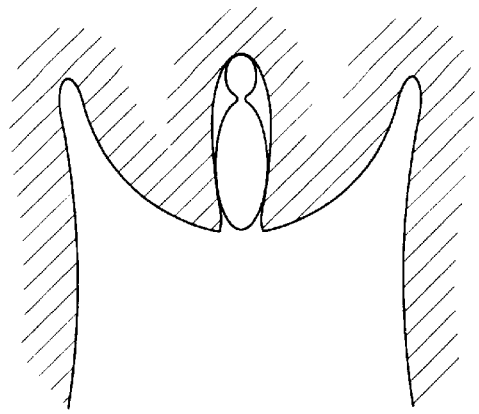
FIG. 6 is a cross-sectional view of a wearer's body surrounding and including the wearer's labia majora and labia minora showing how a prior art interlabial device might fit in the space between the wearer's labia when the wearer is standing.

A. The Absorbent Device.

The present invention is directed to an interlabial absorbent article (or "absorbent interlabial structure" or "absorbent interlabial device") which has a body-contacting surface that is pre-lubricated to prevent drying of the wearer's labial tissue and to reduce friction of the structure against the wearer's labial tissue. FIGS. 1–3 show one preferred embodiment of the interlabial absorbent structure of the present invention, interlabial device 20. The present invention, however, can be in many other forms, and is not limited to a structure having the particular configuration shown in the drawings.

As used herein the term "absorbent interlabial device" refers to a structure which has at least some absorbent components, and is specifically configured to reside at least partially within the interlabial space of a female wearer during use. Preferably, more than one-third, more preferably more than half of the entire absorbent interlabial device 20 of the present invention resides within such interlabial space, more preferably still substantially the entire absorbent interlabial device 20 resides within such interlabial space, and most preferably the entire absorbent interlabial device 20 resides within such interlabial space of a female wearer during use.

As used herein, the term "interlabial space" refers to that space in the pudendal region of the female anatomy which is located between the inside surfaces of the labia majora extending into the vestibule. Located within this interlabial space are the labia minor, the vestibule and the principal urogenital members including the clitoris, the orifice of the urethra, and the orifice of the vagina. Standard medical authorities teach that the vestibule refers to the space bounded laterally by the inside surfaces of the labia minora and extending interiorly to the floor between the clitoris and the orifice of the vagina. Therefore, it will be recognized that the interlabial space as defined above may refer to the space between the inside surfaces of the labia majora, including the space between the inside surfaces of the labia minora also known as the vestibule. The interlabial space for purposes of the present description does not extend substantially beyond the orifice of the vagina into the vaginal interior.

The term "labia" as used herein refers generally to both the labia majora and labia minora. The labia terminate anteriorly and posteriorly at the anterior commissure and the posterior commissure, respectively. It will be recognized by those skilled in the art that there is a wide range of variation among women with respect to the relative size and shape of labia majora and labial minora. For purposes of the present description, however, such differences need not be specifically addressed. It will be recognized that the disposition of the absorbent interlabial device into the interlabial space of a wearer as defined above will require placement between the inside surfaces of the labia majora without regard to the precise location of the boundary between the labia majora and the labia minora for a particular wearer. For a more detailed description of this portion of the female anatomy, attention is directed to Gray's Anatomy, Running Press 1901 Ed. (1974), at 1025–1027.

The absorbent interlabial device 20 shown in FIG. 1 has a longitudinal centerline L which runs along the "x" axis shown in FIG. 1. The term "longitudinal", as used herein, refers to a line, axis or direction in the plane of the interlabial device that is generally aligned with (e.g., approximately parallel to) a vertical plane which bisects a standing wearer into left and right body halves when the interlabial device 20 is worn. The terms "transverse," "lateral," or "y direction" as used herein, are interchangeable, and refer to a line axis or direction that is generally perpendicular to the longitudinal direction. The lateral direction is shown in FIG. 1 as the "y" direction. The "z" direction, shown in FIG. 1, is a direction parallel to the vertical plane described above. The term "upper" refers to an orientation in the z-direction toward the wearer's head. "Lower" or downwardly is toward the wearer's feet.

As shown in FIG. 1, the interlabial device 20 comprises a main absorbent portion (or "central absorbent") 22, and a pair of flexible extensions 24 joined to the main absorbent portion 22. The main absorbent portion 22 should be at least partially absorbent. The main absorbent portion 22 may comprise non-absorbent portions, such as a liquid impervious barrier to prevent absorbed exudates from leaking out of the main absorbent portion 22. The main absorbent portion 22 comprises an upper portion 26 and a lower portion 28 that is opposed to the upper portion. The flexible extensions 24 are joined to the upper portion 26 of the main absorbent portion. In use, the upper portion 26 is positioned furthest inward into the wearer's interlabial space. The interlabial device has a body-facing (or "body-contacting") surface 20A and a back surface 20B. The body-facing surface 20A can be comprised of at least a portion of the absorbent portion 22, at least a portion of the flexible extensions 24, or at least a portion of both.

The interlabial device 20 should be of a suitable size and shape that allows at least a portion thereof to fit comfortably within the wearer's interlabial space and to cover the wearer's vaginal orifice, and preferably also the wearer's urethra. The interlabial device 20 at least partially blocks, and more preferably completely blocks and intercepts the flow of menses, urine, and other bodily exudates from the wearer's vaginal orifice and urethra.

The size of the interlabial device 20 is also important to the comfort associated with wearing the device. In the preferred embodiment shown in FIG. 1, the main absorbent portion 22 of the interlabial device 20 has a length as measured along the longitudinal centerline, L, of between about 35 mm and about 100 mm. Preferably, the length of the interlabial device 20 is between about 45 mm and about 55 mm, and more preferably, is about 49 mm. The caliper (or width) of the main absorbent portion 22 of the interlabial device as measured in the transverse direction (or "y"-direction) is preferably less than or equal to about 8 mm, more preferably the caliper is between about 3 mm and about 6 mm, most preferably, the caliper is about 4.5 mm. Caliper measurements given herein were measured using an AMES gage with a 0.25 psi (gauge) load and a 0.96 inch diameter foot. Those skilled in the art will recognize that if a 0.96 inch diameter foot is not appropriate for a particular sample size, the foot size may be varied while the load on the gauge is accordingly varied to maintain a confining pressure of 0.25 psi (gauge). The height (or "z" direction dimension) of the main absorbent portion 22 is preferably between about 8 mm and about 35 mm, and more preferably is about 20 mm.

The interlabial device 20 is preferably provided with sufficient absorbency to absorb and retain the exudates discharged from the wearer's body. The capacity of the product, however, is dependent at least partially upon the physical volume of the absorbent interlabial device 20, particularly the main absorbent portion 22 thereof. The main absorbent portion 22 preferably has a capacity of at least about 1 g of 0.9% by weight saline solution, and may have a capacity of up to about 30 g by using absorbent gels or foams that expand when wet. Capacities may typically range from about 2 to about 20 grams, for saline. In particularly preferred embodiments, the interlabial device has a capacity of greater than or equal to about 2.5 grams of saline, and more preferably greater than or equal to about 4 grams of saline. Those skilled in the art will recognize that the capacity for absorption of body exudates such as menses will typically be smaller than the capacities given above for absorption of saline. A method for measuring absorbent capacity is described in the Test Methods section, below. Since the interlabial space can expand, larger volumes can be stored in the interlabial space, if the fluid is stored as a gel, which adjusts to the body pressures. Additionally, if the absorbent interlabial device 20 does not reside completely within the wearer's interlabial space, some of the absorbed exudates may be stored externally to the wearer's interlabial space.

The main absorbent portion 22 of the preferred embodiment shown in FIGS. 1–3 may comprise any suitable type of absorbent structure that is capable of absorbing and/or retaining liquids (e.g. menses and/or urine). The main absorbent portion 22 may be manufactured in a wide variety of shapes. Non-limiting examples include ovoid, trapezoidal, rectangular, triangular, cylindrical, hemispherical or any combination of the above. The main absorbent portion 22 may, likewise, be manufactured and from a wide variety of liquid-absorbent materials commonly used in absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. Preferred absorbent materials comprise folded tissues, woven materials, nonwoven webs, needle punched rayon, and layers or pieces of foam. The main absorbent portion 22 may comprise a single material or a combination of materials, such as a wrapping layer surrounding a central wadding comprised of a different absorbent material.

In the preferred embodiment shown in FIG. 1, the main absorbent portion 22 is formed of a soft absorbent material such as rayon fibers or other suitable natural or synthetic fibers or sheeting. The main absorbent portion 22 shown in FIG. 1 is generally of an ovoid cross sectional shape as shown in FIG. 2. The main absorbent portion 22 of the embodiment shown in FIGS. 1 and 2 comprises an upper portion 26 with a larger transverse sectional dimension relative to that of the lower portion 28. The upper portion 26 is preferably integral with the lower portion 28. In less preferred embodiments, however, the upper portion 26 and lower portion 28 may comprise separate elements joined together by any suitable means know in the art. In the preferred embodiment shown in FIGS. 1 and 2, the juncture of the upper portion 26 and lower portion 28 of the main absorbent portion 22 comprises a substantially abrupt change in the transverse dimension thereby forming a shoulder-like configuration at such juncture. In the preferred embodiment shown in FIGS. 1 and 2, the juncture of the upper portion 26 and lower portion 28 of the main absorbent portion 22 is formed by stitching 34.

In a variation of the preferred embodiment described above and shown in FIGS. 1 and 2, the upper portion 26 may have a smaller transverse sectional dimension relative to the transverse sectional dimension of the lower portion 28. An absorbent interlabial device 20 having such a configuration is shown in FIG. 3.

The main absorbent portion 22 can be made by any suitable process. U.S. Pat. No. 4,995,150 issued to Gerstenberger et al. on Feb. 26, 1991 and U.S. Pat. No. 4,095,542 issued to Hirschman on Jun. 20, 1978 describe methods for making absorbent devices which are suitable for use as the main absorbent portion 22 of the absorbent interlabial device 20 shown in FIGS. 1–3.

As shown in FIGS. 1–3, a preferred embodiment of the absorbent interlabial device 20 also comprises a pair of flexible extensions 24 which are joined to the upper portion 26 of the main absorbent portion 22 of the absorbent interlabial device 20. In the preferred embodiment shown in FIGS. 1–3, the flexible extensions 24 are generally rectangular in shape. Other shapes are also possible for the flexible extensions 24 such as semi-circular, trapezoidal, or triangular. The flexible extensions 24 preferably are from about 30 mm to about 160 mm in length, more preferably from about 45 mm to about 130 mm in length, and most preferably from about 50 mm to about 115 mm in length. While the flexible extensions 24 can have a length (measured in the x-direction) which is shorter than the main absorbent portion 22, preferably they have a length which is the same as or longer than the main absorbent portion 22 of the absorbent interlabial device 20. The width of each flexible extensions refers to the distance from the attachment of flexible extension 24 to the main absorbent portion 22 (or the proximal end 24A of the flexible extension 24) to the distal end (or free end) 24B of the flexible extension 24. The width of the flexible extensions 24 is preferably about equal to or greater than the height of the main absorbent portion as described above. The caliper of the flexible extensions is preferably less than or equal to about 3 mm, more preferably less than or equal to about 2 mm, and most preferably less than or equal to about 1 mm. Ideally, the caliper of the flexible extensions 24 and the main absorbent portion 22 are selected such that the caliper of the overall absorbent interlabial structure 20 is less than or equal to about 8 mm.

The flexible extensions 24 may be constructed of a tissue layer. A suitable tissue is an airlaid tissue available from Fort Howard Tissue Company of Green Bay, Wis., and having a basis weight of 35 lbs./3000 sq. ft. Another suitable airlaid tissue is available from Merfin Hygenic Products, Ltd., of Delta, British Columbia, Canada, having a basis weight of 61 g/m$^2$ and having the designation grade number 176. Still another suitable material is an airlaid cotton batt such as that sold as cosmetic squares by Revco Stores, Inc. of Twinsberg, Ohio. The flexible extensions 24 may optionally be backed with a layer of material which is impervious or semi-pervious to body exudates such as, polyethylene, polypropylene, or a polyvinylalchohol.

In the preferred embodiments shown in FIGS. 1–3 the pair of flexible extensions 24 may comprise a single sheet of material extending to either side of the longitudinal centerline L of the main absorbent portion 22 of the absorbent interlabial device 20. Alternatively, the pair of flexible extensions 24 may comprise separate sheets of material independently joined to the upper portion 26 of the main absorbent portion 22. Preferably, the flexible extensions 24 are arranged symmetrically about the longitudinal centerline L of the main absorbent portion 22. The flexible extensions 24 are joined to the upper portion 26 of the main absorbent portion 22 of the absorbent interlabial device 20. Most preferably, the flexible extensions are joined to the top surface of the upper portion 26 of the main absorbent portion 22, or within about 3 mm of the top surface of the main absorbent portion 22.

The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element; i.e., one element is essentially part of the other element.

The flexible extensions 24 may be joined to the upper portion 26 of the main absorbent portion 22 by any variety of means. For example, in the preferred embodiments shown in FIGS. 1–3 the flexible extensions 24 may be joined to the upper portion 26 using any suitable adhesive 36 centered about the longitudinal centerline L of the main absorbent portion 22 (i.e., on opposite sides of the longitudinal centerline L). The adhesive 36 may extend continuously along the length of the main absorbent portion 22 or it may be applied in a "dotted" fashion at discrete intervals. Alternatively, the flexible extensions 24 may be joined to the upper portion 26 of the main absorbent portion 22 by stitching (such as with cotton or rayon thread), thermally bonding, fusion bonding, or any other suitable means known in the art for joining such materials.

Figure 9:
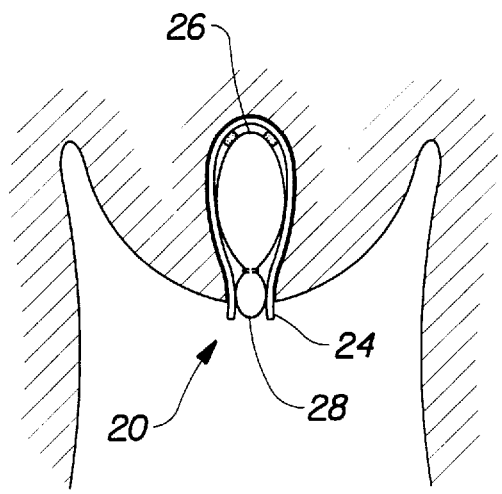
FIG. 9 is a cross-sectional view of the same region of the wearer's body shown in FIG. 6 showing how the absorbent interlabial device of the present invention fits when the wearer is standing.

As shown in FIGS. 1–3, the flexible extensions 24 are attached to the upper portion 26 of the main absorbent portion 28. The flexible extensions 24 extend downwardly and outwardly from the main absorbent portion 22 to a free end 24B which is unattached to the main absorbent portion. The flexible extensions 24 may be biased slightly outward from the main absorbent portion 22 so as to tend to keep the extensions 24 in contact with the inner surfaces of the labia when the absorbent interlabial device 20 is in place. Additionally, the naturally moist surfaces of the labia will have a tendency to adhere to the material comprising the flexible extensions 24 further tending to keep them in contact with the inner surfaces of the labia. Preferably the flexible extensions 24 should be capable of motion from a position where the free ends of the flexible extensions 24 lie adjacent to the main absorbent portion 22 (as shown in FIG. 9) to a position where the flexible extensions 24 extend directly out from the main absorbent portion 22 in the transverse direction (as shown in FIG. 4).

Figure 8:
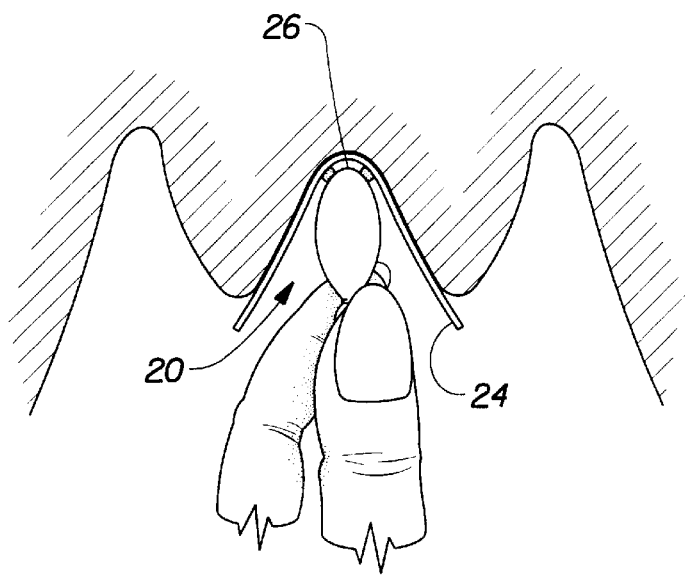
FIG. 8 is a cross-sectional view of the same region of the wearer's body shown in FIG. 7 showing the flexible extensions of the present invention covering the wearer's fingertips as the absorbent device of the present invention is inserted into the wearer's interlabial space.

The flexible extensions 24 should be of sufficient width and flexibility to allow the flexible extensions to cover the wearer's fingertips as the absorbent interlabial device 20 is inserted into the wearer's interlabial space. FIG. 8 shows how a wearer may grasp the main absorbent portion 22 of the absorbent interlabial device 20 while the flexible extensions 24 remain between the wearer's fingers and her body as the device 20 is inserted. Additionally, the flexible extensions 24 should be capable of moving with the inner surfaces of the wearer's labia to maintain contact with the same. The flexible extensions 24 help keep the main absorbent portion 22 in place throughout a range of wearer motions such as squatting.

The flexible extensions may be hydrophilic or hydrophobic. The flexible extensions 24 may be treated to make them less hydrophilic than the main absorbent portion 22. The hydrophilicity of a material is generally expressed in terms of its contact angle. Thus, the flexible extensions 24 may have an advancing contact angle greater than the advancing contact angle of the main absorbent portion 22, such that fluid is preferentially directed toward and absorbed by the main absorbent portion 22. The flexible extensions 24 may be either absorbent or non-absorbent. Preferably, the flexible extensions 24 have at least some absorbency. However, the majority of the fluid absorbed and retained by the absorbent interlabial device 20 will preferably ultimately be retained in the main absorbent portion 22. For a more detailed description of hydrophilicity and contact angles see the following publications which are incorporated by reference herein: The American Chemical Society Publication entitled "Contact Angle, Wettability, and Adhesion," edited by Robert F. Gould, and copyrighted in 1964; and TRI/Princeton Publications, Publication Number 459, entitled "A Microtechnique for Determining Surface Tension," published in April 1992, and Publication Number 468 entitled, "Determining Contact Angles Within Porous Networks," published in January, 1993, both edited by Dr. H. G. Heilweil.

The stiffness of both the main absorbent portion 22 and the flexible extensions 24 is important for product comfort. If the main absorbent portion 22 is too flexible, the device is not conveniently or easily placed between the folds of the labia, if it is too stiff, the device is uncomfortable and when the user is in a sitting position, the product can be forced forward against the clitoris causing discomfort. The main absorbent portion 22 preferably has a stiffness approximately equal to that of the products described in U.S. Pat. Nos. 4,995,150 and 4,095,542.

The strength and stiffness of the flexible extensions 24 are important characteristics of their design. If the flexible extensions 24 have a wet burst strength of about less than or equal to 15 grams, they will tend to shred and may leave pieces remaining in the wearer's interlabial space. Similarly, if the flexible extensions 24 are as stiff as a manila file folder, they do not provide sufficient flexibility to dynamically adjust to the motion of the labia. The stiffness of the flexible extensions is measured as a bending resistance. Preferably, the flexible extensions 24 have a bending resistance of less than about 25 gm measured using the Three Point Bend Test. More preferably, the flexible extensions 24 have a bending resistance of less than or equal to about 5 gm. A description of the Three Point Bend Test is contained in the Test Methods section, below. The flexible extensions 24 also have an inherent strength, so that during application and wear they do not tear. The wet strength for the flexible extensions should exceed 15 grams, and preferably exceeds 150 grams, and most preferably exceeds 300 grams. The wet strengths given above are measured using the Wet Burst Test which is described in greater detail in the Test Methods section, below.

In an alternative preferred embodiment shown in FIG. 4, the main absorbent portion 22 of the absorbent interlabial device 20 comprises a pleated structure. As shown in FIG. 4, the main absorbent portion 22 comprises a folded tissue web. The folded tissue web preferably has a strength greater than that of standard non-wet strength toilet tissue. Preferably, the main absorbent portion 22 comprises a tissue having a temporary wet strength of greater than or equal to about 100 g. In a preferred design this wet strength will decay to about 50% or less of the original strength over about 30 minutes.

As shown in FIG. 4, the tissue web comprising the main absorbent portion 22 is folded into a pleated structure comprising a plurality of pleats 30 that are arranged in a laterally side-by-side relationship. The tissue web can be folded so that it has any suitable number of pleats. Preferably, the tissue web is folded so that the overall caliper (i.e., the width) of the main absorbent portion 22 of this embodiment is between about 2 mm and less than or equal to about 7 mm.

The pleats in the folded tissue web are preferably connected or joined (or retained) in some suitable manner so that the pleated sections maintain their pleated configuration, and are not able to fully open. The pleats can be connected by a variety of means including the use of thread, adhesives, or heat sealing tissues which contain a thermoplastic material, such as, polyethylene. A preferred design uses stitching which joins all of the pleats in the main absorbent portion 22 together. Preferably, the main absorbent structure 22 is provided with five stitch locations (four at the corners and one additional location approximately midway between the two lower corners).

The pleated structure of the main absorbent portion 22 provides several advantages. One advantage provided by the pleated structure is that exudates can penetrate into the pleats of the structure which present a larger and more effective absorbent surface for acquisition than a flat surface. This is particularly important when dealing with potentially viscous fluids and particulate material such as cellular debris and clots which can plug the surface of the structure presented to the body. A second advantage of this design is that the caliper (or width) of the product can be easily and conveniently controlled by varying the number of pleats. The structure shown in FIG. 4 also provides a convenient central zone for grasping the product and inserting into the labia, while the body/fingers on the inserting hand are protected from contacting the wearer's body.

As noted above for the preferred embodiment shown in FIGS. 1–3, the flexural rigidity of the main absorbent portion 22 is also important for product comfort with the pleated structure shown in FIG. 4. An advantage of the pleated structure is that the number, thickness, and tightness of the pleats control the stiffness of the structure.

The preferred embodiment shown in FIG. 4, preferably has main absorbent portion 22 and flexible extension 24 dimensions similar to those described above for the embodiment shown in FIGS. 1–3. The width of the main absorbent portion 22 of the interlabial device 20 as measured in the transverse direction (y-direction) is preferably between about 2 mm and less than or equal to about 7 mm. Preferably, in a preferred embodiment, the width of the main absorbent portion of the interlabial device 20 is about 4.5 mm. As shown in FIG. 4, where the main absorbent portion 22 is of a uniform transverse dimension (i.e., there is no abrupt change in transverse dimension defining the juncture between the upper portion and lower portion) the division between the upper portion 26 and lower portion 28 is considered to be at a height equal to about one-half of the total height of the main absorbent portion 22.

The pleated design shown in FIG. 4 has the additional benefit of easily providing the flexible extensions 24. The extensions 24 can comprise the same material as the main absorbent portion 22, or they can comprise a different material. The extensions 24 are joined to the upper portion 26 of the main absorbent portion 22, and most preferably, for this embodiment, are joined to the top surface of the main absorbent portion 22, or within 2 millimeters of the top surface of the main absorbent portion 22. Preferably, in the embodiment shown in FIG. 4, the extensions 24 are integral portions of the main absorbent portion 22 (that is, the extensions 24 comprise integral extensions of the absorbent tissue material that is folded to form the main absorbent portion 22.

The main absorbent portion 22 and the flexible extensions 24 of the absorbent interlabial device 20 shown in FIG. 4 may be constructed from any of the materials previously discussed for the embodiments shown in FIGS. 1–3.

The embodiment shown in FIG. 4 can be provided with various optional features. For example, there may be spacers or high loft or void zones between the pleats to improve the ability of the device 20 to move exudates downward. Additionally, the pleats on the portion of the product contacting the pelvic floor do not need to be of uniform height. For example, the pleated material in the center might be higher and, therefore, easily collapsed under pressure. Such an arrangement can provide better fit and/or comfort.

In another variation of the pleated structure shown in FIG. 4, the main absorbent portion 22 may comprise a plurality of individual layers 32 joined in a face-to-face relationship. Such a device is shown in FIG. 5. The structure shown in FIG. 5 may have all of the same characteristics described above for the pleated structure. One benefit of the use of a plurality of individual layers 32 is that the various layers may comprise different materials with different properties or characteristics. Each of the flexible extensions 24 may be integral with one of the individual layers 32 or may be joined separately to the upper portion 26 of the main absorbent portion 22. Preferably, the individual layers 32 are arranged in a side-by-side relationship so that the spaces between the layers are oriented in the z-direction (as shown in FIG. 5).

The interlabial device 20 in any of the embodiments shown in the drawings may comprise other optional components. For example, the interlabial device 20 may comprise a topsheet 42 positioned over and joined to all or a portion of the body-facing surface of the device 20 and/or a backsheet 38 positioned over and joined to all or a portion of its back surface, including the flexible extensions 24. Preferably, if a topsheet 42 and/or a backsheet 38 is used, these components are joined to at least a portion of the main absorbent portion. In an alternative embodiment, the main absorbent portion could be at least partially wrapped by a topsheet 42.

If a topsheet is used, the topsheet should be compliant, soft feeling, and non-irritating to the wearer's skin. Further, the topsheet should be liquid pervious permitting liquids (e.g., menses and/or urine) to readily penetrate through its thickness. A suitable topsheet may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, rayon, polypropylene, or polyethylene fibers) or from a combination of natural and synthetic fibers.

The topsheet may comprise an apertured formed film. Apertured formed films are pervious to body exudates and, if properly apertured, have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec.30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. The preferred topsheet for the present invention is the formed film described in one or more of the above patents and marketed on sanitary napkins by The Procter & Gamble Company of Cincinnati, Ohio as the "DRI-WEAVE" topsheet.

In a preferred embodiment of the present invention, the body surface of the formed film topsheet is hydrophilic so as to help liquid to transfer through the topsheet faster than if the body surface was not hydrophilic so as to diminish the likelihood that menstrual fluid will flow off the topsheet rather than flowing into and being absorbed by the main absorbent portion 22. In a preferred embodiment, surfactant is incorporated into the polymeric materials of the formed film topsheet. Alternatively, the body surface of the topsheet can be made hydrophilic by treating it with a surfactant such as is described in U.S. Pat. No. 4,950,254 issued to Osborn.

If a backsheet is used, the backsheet could be impervious or semi-pervious to liquids (e.g., menses and/or urine) and is preferably flexible. As used herein, the term "flexible" refers to materials which are compliant and will readily conform to the general shape and contours of the human body. The backsheet prevents the exudates absorbed and contained in the main absorbent portion 22 from wetting articles which contact the absorbent interlabial device 20 such as the wearer's undergarments. The backsheet also assists the main absorbent portion 22 in preventing the wearer's body from being soiled by exudates. Additionally, use of the backsheet may provide an improved surface for the wearer to grasp between the fingers as the absorbent interlabial device 20 is inserted, or as the device is optionally removed with the fingers.

The backsheet may comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). An exemplary polyethylene film is manufactured by Clopay Corporation of Cincinnati, Ohio, under the designation P18-0401. The backsheet may permit vapors to escape from the main absorbent portion 22 (i.e., breathable) while still preventing exudates from passing through the backsheet.

As previously discussed, the absorbent interlabial device 20 of the present invention is preferably designed to be placed entirely within the interlabial space of a wearer. To use the absorbent interlabial device 20 of the present invention, the wearer holds the main absorbent portion 22 between her fingers. As shown in FIG. 8, the flexible extensions 24 are spread apart so as to cover the tips of the wearer's fingers during insertion. This feature provides for a hygienic insertion of the absorbent interlabial device 20 of the present invention. The upper portion 26 is inserted first and furthest into the interlabial space. The wearer may assume a squatting position during insertion to assist in spreading the labial surfaces. Once the absorbent interlabial device 20 is inserted, the flexible extensions 24 tend to adhere to the inside surfaces of the labia. When the wearer is standing, the labial walls close more tightly around the absorbent interlabial device 20 as shown in FIG. 9.

Figure 12:
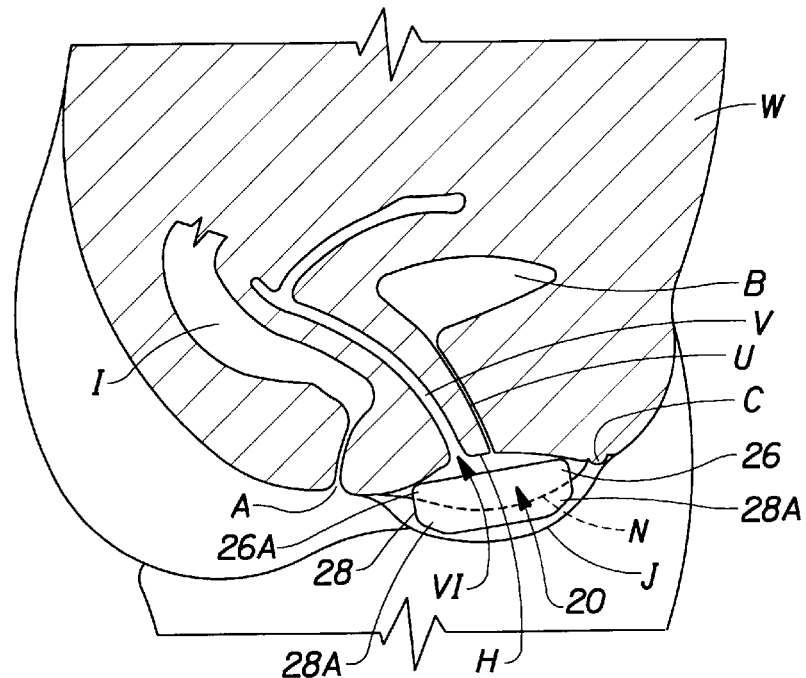
FIG. 12 is a sectional view of the wearer's body showing how the emollient-treated interlabial device of the present invention may fit.

FIG. 12 shows the interlabial device 20 in place in a wearer's body. The parts of the wearer's body, W, shown in FIG. 12 are designated as follows: bladder, B, clitoris, C, urethra, U, labia minora, N, labia majora, J, vagina, V, vaginal introitus, VI, anus, A, hymenal ring, H, and large intestine, I. The interlabial device 20 is inserted so that it is worn between the wearer's labia minora N and labia majora J and blocks the wearer's vaginal introitus VI without entering the vagina past the hymenal ring H. That is, the interlabial device 20 lies at least partially in the vestibule bounded by the labia minora when such device is worn. The interlabial device 20 may also cover, but does not necessarily occlude, the wearer's urethra U. Preferably, the interlabial device 20 covers both the wearer's vaginal introitus VI and the wearer's urethra U. Ideally, the interlabial device 20 is maintained in contact with as large a portion of the inner surface area of the wearer's labia minora N and labia majora J as possible. This will ensure that the interlabial device 20 intercepts as much of the wearer's body exudates as possible. Preferably, the entire interlabial device 20 is intended to be worn below the wearer's hymenal ring H.

The interlabial device 20 may also contain a portion that is worn outside the wearer's labia majora J. This portion could, for example, be used for storage of body exudates that are transferred from the portion of the interlabial device 20 that is worn between the wearer's labia minora and labia majora. The portion of the interlabial device 20 that is worn between the wearer's labia minora and labia majora will, as a result, will have exudates drained therefrom, and be able to receive additional loadings of body exudates.

The interlabial device 20 is preferably at least partially retained in place by exerting a slight laterally outwardly-oriented pressure on the inner surfaces of the wearer's labia minora, labia majora, or both. Additionally, the product is also held by attraction of naturally moist labial surfaces to the tissue comprising the flexible extensions 24. Optionally, the flexible extensions 24 may be provided with a biocompatible adhesive to assist the adhesion of the flexible extensions 24 to the inside surfaces of the wearer's labia. The strength of such an adhesive should be selected to assist the absorbent interlabial device 20 in staying in place, while still allowing for reliable, and comfortable removal of the device from the wearer's interlabial space.

Figure 7:
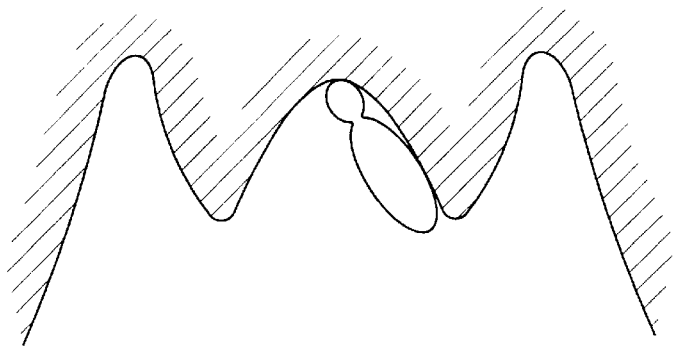
FIG. 7 is a cross-sectional view of the same region of the wearer's body shown in FIG. 6 showing how the prior art device might fit when the wearer squats.
Figure 10:
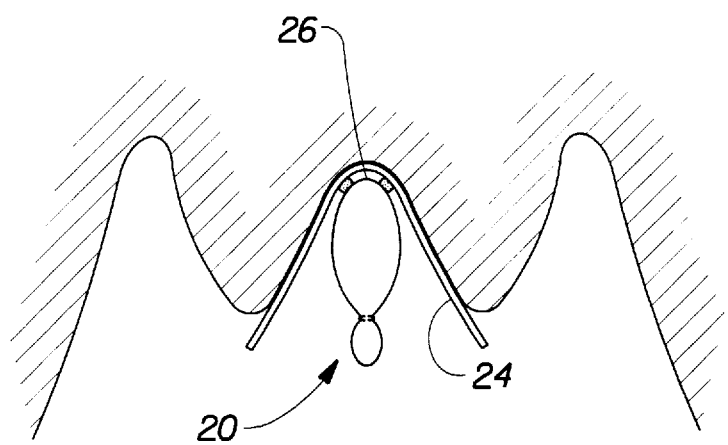
FIG. 10 is a cross-sectional view of the same region of the wearer's body shown in FIG. 7 which shows how the absorbent interlabial device of the present invention fits when the wearer squats.

The absorbent interlabial device 20 is believed to differ from the prior art in a number of respects. FIG. 6 shows a prior art interlabial device positioned within the interlabial space when the wearer is standing. When the wearer squats, however, the labia tend to separate as shown in FIGS. 7 and 10. The prior art device may tend to shift to one side or another in such a situation (as shown in FIG. 7). If the wearer urinates when the prior art device is in the position shown in FIG. 7, the stream of urine will completely miss the device. The flexible extensions 24 of the present invention, however, are adapted to maintain contact with the inside surfaces of the labia in order to keep the absorbent interlabial device 20 in proper position (as shown in FIG. 10). This action of the flexible extensions 24 is believed to keep the absorbent interlabial device 20 of the present invention in a position which more consistently blocks the orifice of the urethra than the prior art device. As a result, the absorbent interlabial device 20 of the present invention is believed to be expelled by urination more reliably than the prior art device. As noted previously, the flexible extensions 24 also cover the wearer's fingertips during insertion (as shown in FIG. 8) thereby providing for a more hygienic insertion than is achieved with the prior art device. Optionally, the absorbent interlabial device 20 may be removed by grasping the lower portion 28 of the main absorbent portion 22 with the fingers. Again, the flexible extensions 24 continue to cover the fingertips thereby allowing for a more hygienic removal of the absorbent interlabial device 20 than is achieved with the prior art device.

The absorbent interlabial device 20 can be worn as a "stand alone" product. Alternatively, it can be worn as a back up to a tampon, or in combination with a sanitary napkin, pantiliner, or incontinence pad for menstrual or incontinence use. If the absorbent interlabial device 20 is used with a sanitary napkin, the sanitary napkin can be of any thickness. Use with a sanitary napkin may be preferred at night to reduce rear soiling. The interlabial device 20 can be worn in conventional panties, or it can be used with menstrual shorts.

Numerous alternative embodiments of the absorbent interlabial device of the present invention are possible. For example, these products are designed to be removed by urination, although an alternative extraction string or loop may be used. These products may also be used with medicinal treatments. These products may be constructed of materials which are biodegradable and/or which will fragment in water with agitation (as in a toilet).

Preferably, the absorbent interlabial device 20 is flushable. As used herein the terms "flushable and flushability" refer to a product's ability to pass through typical commercially available household toilets and plumbing drainage systems without causing clogging or similar problems that can be directly associated with the physical structure of the product. It is recognized, however, that there can be many differences between the various types of toilets available. Therefore, for the purposes of the appended claims, a test to determine the flushability of a catamenial product, such as an interlabial device, is set out in the TEST METHODS section of this specification.

The absorbent interlabial device 20 may also be constructed with a plurality of slits in the main absorbent portion 22 so as to permit bending of the product in multiple independent directions. Such a structure allows the product to more easily respond to the stresses associated with body movements. As shown in FIG. 12, in preferred versions of any of the embodiments shown in the prior drawing figures, the upper corner portions 26A and the lower corner portions 28A of the interlabial device 20 may be rounded to reduce the forces that the product transfers to the wearer's body when the wearer sits down. The top surface of the structure may also have one or more slits or have other regions of preferred bending so that product may easily adjust to the vertical pressure against the pelvic floor, to help accommodate the non-linear surface of the pelvic floor between the clitoris and the perineum.

The flexible extensions 24 of the absorbent devices above may also act as a spring in both wet and dry conditions such that the sides of the product tend to expand outward pressing against the lateral walls of the labial vestibule, thereby, holding the product in place. In addition, it is preferred that the flexible extensions 24 maintain the ability to act as a "spring" when wet, such as when the product is saturated with liquid. Structures, such as polyurethane foams can provide these properties.

B. The Emollient Composition

The emollient compositions used on the interlabial device of the present invention may be solid, liquid, or semisolid at 20° C., i.e. at ambient temperatures. Preferably, the emollient compositions have a semisolid consistency that can be described as an unctuous jelly-like consistency at 20° C. By "semisolid" is meant that the emollient composition has a rheology typical of pseudoplastic or plastic fluids. The term "fluid", as used herein, means liquid (as opposed to gas). The physical states of the emollient composition and the components thereof, described herein refer to their states at any time after the product is manufactured and the emollient composition is applied to the product. Thus, for the purpose of the appended claims, the device will be considered to be in the claimed state when the device is in storage, on store shelves or in use, etc. When no shear is applied, the emollient compositions described herein can have the appearance of a semi-solid but can be made to flow as the shear rate is increased. This is due to the fact that, while the emollient composition contains primarily solid components, it also includes some minor liquid components.

By being solid or semisolid at ambient temperatures, these emollient compositions do not have a tendency to flow and migrate into the interior of the absorbent interlabial device to which they are applied. This also allows less emollient composition to be used for imparting softness and smoothing benefits.

When applied to the body-contacting surface of the interlabial device 20, the emollient compositions described herein impart a soft, lubricious, smooth feeling to the user of the device. This particular feel has also been characterized as "silky", "slick", "smooth", etc.

The emollient compositions of the present invention preferably comprise: (1) an emollient(s); (2) an immobilizing agent(s) for the emollient; (3) optionally a hydrophilic surfactant(s), and (4) other optional components.

1. Emollient

The key active ingredient in these emollient compositions is one or more emollients. As used herein, an emollient is a material that smoothes, softens, soothes, supples, coats, lubricates, moisturizes, or cleanses the skin and/or mucous membranes. An emollient typically accomplishes several of these objectives such as soothing, moisturizing, and lubricating the skin. For the purposes of the present invention, these emollients have either a semi-solid, a plastic, or a fluid consistency at 20° C., i.e., at ambient temperatures. By "plastic consistency" is meant that the emollient behaves as a non-Newtonian liquid which can be made to flow when a sufficient shear rate is applied thereto. By "fluid consistency" is meant that the emollient behaves as a Newtonian liquid which flows immediately when stressed, with the the rate of flow being proportional to the stress. The plastic or fluid emollient consistency allows the emollient composition to impart a soft, lubricious, smoothing feel.

The emollients will, therefore, preferably have a softening point at body temperature, 98.6° F. (37° C.). (Body temperature will be slightly less in the area of a female wearer's labial vestibule.) Preferably, the emollient composition has at least one component with a peak heat absorption of less than 99° F. (37° C.). This will ensure that at least part of the components will melt below body temperature to provide a more fluid feel and reduced friction against the body. Peak heat absorption can be measured using a differential scanning calorimeter. In addition, in preferred embodiments, the emollients will soften over a span of temperatures, rather than having a sharp transition at which it changes from a solid to a liquid. For example, the emollients may begin to soften at about 20° C., or less, and be approximately 80% melted ("melted", as used herein, means completely liquid) at 38° C. (about 100° F.). This will provide the emollient coated device with a lubricious feel at body temperatures which will increase as it adjusts from ambient temperature to body temperature.

The emollients used in the present invention preferably do not contain any high molecular weight hydrocarbon components. If the emollients used herein contain hydrocarbon components, the molecular weights of such components are preferably less than 1,500, more preferably less than or equal to about 1,400, and most preferably less than or equal to about 1,200. Such emollients will provide more soothing or lotion-like benefits to the wearer's skin than high molecular weight materials. They will also be capable of transferring to the wearer's skin to provide skin care benefits unlike high molecular weight materials. In addition, they will remain flexible when the interlabial device flexes and bends, and will not tend to flake or chip off the interlabial device.

The emollients useful in the present invention are also substantially free of water. Preferably, the oeverall emollient composition is also substantially free of water. By "substantially free of water" it is meant that water is not intentionally added to the emollient and/or emollient composition. Addition of water to the emollient and/or emollient composition is not necessary in preparing or using the emollient compositions on the present invention and could require an additional drying step. However, minor or trace quantities of water in the emollient and/or emollient composition that are picked up as a result of, for example, ambient humidity can be tolerated without adverse effect. Typically, the emollients and or emollient compositions used in the present invention contain about 10% or less water, preferably 5% or less water, more preferably about 1% or less water, and most preferably about 0.5% or less water.

Emollients useful in the present invention can be petroleum-based, fatty acid ester type, alkyl ethoxylate type, fatty acid ester ethoxylates, fatty alcohol type, or mixtures of these emollients. Suitable petroleum-based emollients include those hydrocarbons, or mixtures of hydrocarbons, having chain lengths of from 16 to 32 carbon atoms. Petroleum based hydrocarbons having these chain lengths include mineral oil (also known as "liquid petrolatum") and petrolatum (also known as "mineral wax," "petroleum jelly" and "mineral jelly"). Mineral oil usually refers to less viscous mixtures of hydrocarbons having from 16 to 20 carbon atoms. Petrolatum usually refers to more viscous mixtures of hydrocarbons having from 16 to 32 carbon atoms. Petrolatum is a particularly preferred emollient for emollient compositions for use on the interlabial device of the present invention. Petrolatum has a molecular weight of between about 600 and about 700.

Suitable fatty acid ester type emollients include those derived from $C_{12}$–$C_{28}$ fatty acids, preferably $C_{16}$–$C_{22}$ saturated fatty acids, and short chain ($C_1$–$C_8$, preferably $C_1$–$C_3$) monohydric alcohols. Representative examples of such esters include methyl palmitate, methyl stearate, isopropyl laurate, isopropyl myristate, batyl myristate, batyl stearate, octyl palmitate, isopropyl isostearate, isopropyl palmitate, ethylhexyl palmitate and mixtures thereof. Suitable fatty acid ester emollients can also be derived from monoesters and diesters of both short chain ($C_1$ to $C_{10}$) and longer chain fatty alcohols ($C_{12}$–$C_{28}$, preferably $C_{12}$–$C_{16}$) and shorter chain organic acids e.g., lactic acid, such as lauryl lactate and cetyl lactate. Additional examples include diisopropyl sebacate, dimethyl sebacate, dioctyl sebacate, dibutyl sebacate, diisopropyl adipate, and dicapryl adipate. In addition, mixtures of petroleum based emollients and fatty acid ester emollients, if mixed in the right proportions, can sometimes provide emollients systems that have a superior feel compared to the pure components individually.

Suitable alkyl ethoxylate type emollients include $C_{12}$–$C_{22}$ fatty alcohol ethoxylates having an average degree of ethoxylation of from about 2 to about 30. Preferably, the fatty alcohol ethoxylate emollient is selected from the group consisting of lauryl, cetyl, and stearyl ethoxylates, and mixtures thereof, having an average degree of ethoxylation ranging from about 2 to about 23. Representative examples of such alkyl ethoxylates include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) steareth-10 (a stearyl alcohol ethoxylate having an average degree of ethoxylation of 10), and ceteareth-10 (a mixture of cetyl and stearyl ethoxylates having an average degree of ethoxylation of 10). These alkyl ethoxylate emollients are typically used in combination with the petroleum-based emollients, such as petrolatum, at a weight ratio of alkyl ethoxylate emollient to petroleum-based emollient of from about 1:1 to about 1:5, preferably from about 1:2 to about 1:4.

Suitable fatty alcohol type emollients include $C_{12}$–$C_{22}$ fatty alcohols, preferably $C_{16}$–$C_{18}$ fatty alcohols. Representative examples include cetyl alcohol and stearyl alcohol, and mixtures thereof. These fatty alcohol emollients are typically used in combination with the petroleum-based emollients, such as petrolatum, at a weight ratio of fatty alcohol emollient to petroleum-based emollient of from about 1:1 to about 1:5, preferably from about 1:1 to about 1:2.

Other suitable types of emollients for use in the present invention include polysiloxane compounds. In general suitable polysiloxane materials for use in the present invention include those having monomeric siloxane units of the following structure:

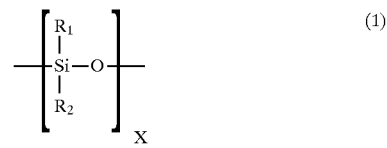

wherein, $R_1$ and $R_2$, for each independent siloxane monomeric unit can each independently be hydrogen or any alkyl, aryl, alkenyl, alkaryl, arakyl, cycloalkyl, halogenated hydrocarbon, or other radical. Any of such radicals can be substituted or unsubstituted. $R_1$ and $R_2$ radicals of any particular monomeric unit may differ from the corresponding functionalities of the next adjoining monomeric unit. Additionally, the polysiloxane can be either a straight chain, a branched chain or have a cyclic structure. The radicals $R_1$ and $R_2$ can additionally independently be other silaceous functionalities such as, but not limited to siloxanes, polysiloxanes, silanes, and polysilanes. The radicals $R_1$ and $R_2$ may contain any of a variety of organic functionalities including, for example, alcohol, carboxylic acid, phenyl, and amine functionalities.

Exemplary alkyl radicals are methyl, ethyl, propyl, butyl, pentyl, hexyl, octyl, decyl, octadecyl, and the like. Exemplary alkenyl radicals are vinyl, allyl, and the like. Exemplary aryl radicals are phenyl, diphenyl, naphthyl, and the like. Exemplary alkaryl radicals are toyl, xylyl, ethylphenyl, and the like. Exemplary aralkyl radicals are benzyl, alpha-phenylethyl, beta-phenylethyl, alpha-phenylbutyl, and the like. Exemplary cycloalkyl radicals are cyclobutyl, cyclopentyl, cyclohexyl, and the like. Exemplary halogenated hydrocarbon radicals are chloromethyl, bromoethyl, tetrafluorethyl, fluorethyl, trifluorethyl, trifluorotloyl, hexafluoroxylyl, and the like.

Viscosity of useful polysiloxanes useful may vary as widely as the viscosity of polysiloxanes in general vary, so long as the polysiloxane is flowable or can be made to be flowable for application to the body-contacting surface of the interlabial device. This includes, but is not limited to, viscosity as low as 5 centistokes (at 37° C. as measured by a glass viscometer) to about 20,000,000 centistokes. Preferably the polysiloxanes have a viscosity at 37° C. ranging from about 5 to about 5,000 centistokes, more preferably from about 5 to about 2,000 centistokes, most preferably from about 100 to about 1000 centistokes. High viscosity polysiloxanes which themselves are resistant to flowing can be effectively deposited upon the body-contacting surface by such methods as, for example, emulsifying the polysiloxane in surfactant or providing the polysiloxane in solution with the aid of a solvent, such as hexane, listed for exemplary purposes only. Particular methods for applying polysiloxane emollients to body-contacting surface are discussed in more detail hereinafter.

Preferred polysiloxanes compounds for use in the present invention are disclosed in U.S. Pat. No. 5,059,282 (Ampulski, et al), issued Oct. 22, 1991, which is incorporated herein by reference. Particularly preferred polysiloxane compounds for use as emollients in the emollient compositions include phenyl-functional polymethylsiloxane compounds (e.g., Dow Corning 556 Cosmetic-Grade Fluid: polyphenylmethylsiloxane and General Electric SF1550) and cetyl or stearyl functionalized dimethicones such as Dow 2502, General Electric SF1632 and Dow 2503 polysiloxane fluids, respectively. In addition to such substitution with phenyl-functional or alkyl groups, effective substitution may be made with amino, carboxyl, hydroxyl, ether, polyether, aldehyde, ketone, amide, ester, and thiol groups. Of these effective substituent groups, the family of groups comprising phenyl, amino, alkyl, carboxyl, and hydroxyl groups are more preferred than the others; and phenyl-functional groups are most preferred.

Cycylic polysiloxane structures can also be effective polysiloxane emollients and are expressly within the scope of the present invention. Examples of preferred cycylic polysiloxane structures include cyclomethicones such as General Electric SF1173, SF1202, SF1204, and SF1214. In addition, nonfunctionalized polysiloxane compounds such as General Electric SF96(100) and SF96(350) can also be used herein and are expressly within the scope of the present invention.

Water-based polysiloxane emulsions that can be sprayed directly onto the body-contacting surface of the interlabial device are also within the scope of the present invention. Examples of suitable water-based polysiloxane emulsions include General Electric SM2169 and SF1318. Because these water-based polysiloxane emulsions can be sprayed directly on to the body-contacting surface of the interlabial device, they offer processing advantages compared to polysiloxanes that need to be mixed with a solvent before application.

Preferably, emollient compositions containing a polysiloxane will further comprise a petroleum based emollient selected from the group consisting of mineral oil, petrolatum, and mixtures thereof. However, the polysiloxanes emollients described above can also be used alone. In fact, emulsion compositions containing 100% polysiloxane emulsions are suitable for use in the present invention.

Besides petroleum-based emollients, fatty acid ester emollients, fatty acid ester ethoxylates, alkyl ethoxylate emollients and fatty alcohol emollients, the emollients useful in the present invention can include minor amounts (e.g., up to about 10% of the total emollient) of other, conventional emollients/solvents. These other, conventional emollients/solvents include propylene glycol, polyethylene glycol, hexylene glycol, di(propylene glycol), glycerine, triethylene glycol, spermaceti or other waxes, fatty acids, and fatty alcohol ethers having from 12 to 28 carbon atoms in their fatty chain, such as stearic acid, propoxylated fatty alcohols; glycerides, acetoglycerides, and ethoxylated glycerides of $C_{12}$–$C_{28}$ fatty acids; other fatty esters of polyhydroxy alcohols; lanolin and its derivatives; silicone polyether copolymers, and polysiloxanes having a viscosity at 20° C. of from about 5 to about 2,000 centistokes such as disclosed in U.S. Pat. No. 5,059,282 (Ampulski et al), issued Oct. 22, 1991, which is incorporated by reference. These other emollients should be included in a manner such that the solid or semisolid characteristics of the emollient composition are maintained.

The amount of emollient that can be included in the emollient composition will depend on a variety of factors, including the particular emollient involved, the emollient-like benefits desired, the other components in the emollient composition and like factors. The emollient composition can comprise from about 5 to about 95% of the emollient. Preferably, the emollient composition comprises from about to about 90% by weight, more preferably from 20 to about 80%, most preferably from about 40 to about 75%, of the emollient.

2. Immobilizing Agent

An optional component of the emollient compositions useful on the interlabial device of present invention is an agent capable of immobilizing the emollient on the surface of the body-contacting surface 20A of the device. Because the emollient in the composition has a plastic or fluid consistency at 20° C., it tends to flow or migrate, even when subjected to modest shear. When applied to an absorbent interlabial device, especially in a melted or molten state, the emollient will not remain primarily on the body-contacting surface of the device. Instead, the emollient will tend to migrate and flow into the interior of the device.

The need for an immobilizing agent is generally greater of the body-contacting surface of the interlabial device comprises an absorbent material, such as cellulose, than it is if the body-contacting surface comprises an apertured plastic film since the apertured film will not tend to absorb the emollient. The immobilizing agent counteracts the tendency of the emollient to migrate or flow by keeping the emollient primarily localized on the body-contacting surface of the absorbent interlabial device. This is believed to be due, in part, to the fact that the immobilizing agent forms hydrogen bonds with any cellulose in the interlabial device. Through this hydrogen bonding, the immobilizing agent becomes localized on the surface of the interlabial device. Since the immobilizing agent is also miscible with the emollient (or solubilized in the emollient with the aid of an appropriate emulsifier), it entraps the emollient on the surface of the absorbent device as well.

It is also advantageous to "lock" the immobilizing agent on the body-contacting surface of the interlabial device. This can be accomplished by using immobilizing agents which quickly solidify (e.g., crystallize) at the surface of the interlabial device. Alternatively, outside cooling of the treated interlabial device by the flow of air over the surface of the device when the device is moving rapidly between stations on a manufacturing line may speed up crystallization of the immobilizing agent. In addition, outside cooling of the treated interlabial device via blowers, fans, etc. can speed up crystallization of the immobilizing agent.

In addition to being miscible with (or solubilized in) the emollient, the immobilizing agent preferably has a melting point of at least about 35° C. This is so the immobilizing agent itself will not have a tendency to migrate or flow. Preferred immobilizing agents will have melting points of at least about 40° C. Typically, the immobilizing agent will have a melting point in the range of from about 50° to about 150° C.

The viscosity of the immobilizing agent should also be as high as possible to keep the emollient from flowing into the interior of the interlabial device. Unfortunately, high viscosities can also lead to emollient compositions that are difficult to apply without processing problems. Therefore, a balance must be achieved so the viscosities are high enough to keep the immobilizing agent localized on the surface of the interlabial device, but not so high as to cause processing problems. Suitable viscosities for the immobilizing agent will typically range from about 5 to about 200 centipoises, preferably from about 15 to about 100 centipoises, measured at 60° C.

Suitable immobilizing agents for the present invention can comprise a member selected from the group consisting of $C_{14}$–$C_{22}$ fatty alcohols, $C_{12}$–$C_{22}$ fatty acids, and $C_{12}$–$C_{22}$ fatty alcohol ethoxylates having an average degree of ethoxylation ranging from 2 to about 30, and mixtures thereof. Preferred immobilizing agents include $C_{16}$–$C_{18}$ fatty alcohols, most preferably selected from the group consisting of cetyl alcohol, stearyl alcohol, and mixtures thereof. Mixtures of cetyl alcohol and stearyl alcohol are particularly preferred. Other preferred immobilizing agents include $C_{16}$–$C_{18}$ fatty acids, most preferably selected from the group consisting of cetyl acid, stearyl acid, and mixtures thereof. Mixtures of cetyl acid and stearyl acid are particularly preferred. Still other preferred immobilizing agents include $C_{16}$–$C_{18}$ fatty alcohol ethoxylates having an average degree of ethoxylation ranging from about 5 to about 20. Preferably, the fatty alcohols, fatty acids and fatty alcohols are linear.

Importantly, these preferred immobilizing agents such as the $C_{16}$–$C_{18}$ fatty alcohols increase the rate of crystallization of the emollient causing the emollient to crystallize rapidly onto the surface of the interlabial device. Lower emollient levels can therefore be utilized or a superior feel can be delivered.

Optionally, other types of immobilizing agents can be used in combination with the fatty alcohols, fatty acids, and fatty alcohol ethoxylates described above. Typically, only minor amounts of these other types of immobilizing agents would be used (i.e., up to about 10% of the total immobilizing agent). Examples of these other types of immobilizing agents includes polyhydroxy fatty acid esters, polyhydroxy fatty acid amides, waxes (preferably waxes having a molecular weight of less than 1,500, more preferably less than or equal to 1,400, and most preferably less than or equal to about 1,200), and mixtures thereof. To be useful as immobilizing agents, the polyhydroxy moiety of the ester or amide should have at least one free hydroxy group. It is believed that these free hydroxy group(s) are the ones that co-crosslink through hydrogen bonds with any cellulosic fibers of the interlabial device to which the emollient composition is applied and homo-crosslink, also through hydrogen bonds, the hydroxy groups of the alcohol, acid, ester or amide, thus entrapping and immobilizing the other components in the emollient matrix. Suitable waxes include, but are not limited to microcrystalline waxes, synthetic waxes, such as polyethylene-type waxes, and silicone waxes.

It is also believed that molecules such as long chain fatty alcohols can orient themselves and interact with one another to form a lamellar structure. In this lamellar structure, the hydroxyl groups and alkyl chains of neighboring alcohol molecules orient and interact with one another to form an organized structure. In this "packing arrangement," the hydroxyl groups of the alcohols form hydrogen bonds with the cellulose polar functionalities (e.g., hydroxy or carbonyl) to "immobilize" the alcohols at the body-contacting surface of the interlabial device. Since the alcohols are miscible with the preferred emollients, anchoring and/or immobilization of the emollient will occur.

Preferred esters and amides will have three or more free hydroxy groups on the polyhydroxy moiety and are typically nonionic in character. Because of the possible skin sensitivity of those using interlabial devices to which the emollient composition is applied, these esters and amides should also be relatively mild and non-irritating to the skin.

Suitable polyhydroxy fatty acid esters for use in the present invention will have the formula:

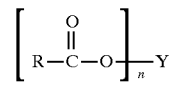

wherein R is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; Y is a polyhydroxyhydrocarbyl moiety having a hydrocarbyl chain with at least 2 free hydroxyls directly connected to the chain; and n is at least 1. Suitable Y groups can be derived from polyols such as glycerol, pentaerythritol; sugars such as raffinose, maltodextrose, galactose, sucrose, glucose, xylose, fructose, maltose, lactose, mannose and erythrose; sugar alcohols such as erythritol, xylitol, malitol, mannitol and sorbitol; and anhydrides of sugar alcohols such as sorbitan.

One class of suitable polyhydroxy fatty acid esters for use in the present invention comprises certain sorbitan esters, preferably the sorbitan esters of $C_{16}$–$C_{22}$ saturated fatty acids. Because of the manner in which they are typically manufactured, these sorbitan esters usually comprise mixtures of mono-, di-, tri-, etc. esters. Representative examples of suitable sorbitan esters include sorbitan palmitates (e.g., SPAN 40), sorbitan stearates (e.g., SPAN 60), and sorbitan behenates, that comprise one or more of the mono-, di- and tri-ester versions of these sorbitan esters, e.g., sorbitan mono-, di- and tri-palmitate, sorbitan mono-, di- and tri-stearate, sorbitan mono-, di and tri-behenate, as well as mixed tallow fatty acid sorbitan mono-, di- and tri-esters. Mixtures of different sorbitan esters can also be used, such as sorbitan palmitates with sorbitan stearates. Particularly preferred sorbitan esters are the sorbitan stearates, typically as a mixture of mono-, di- and triesters (plus some tetraester) such as SPAN 60, and sorbitan stearates sold under the trade name GLYCOMUL-S by Lonza, Inc. Although these sorbitan esters typically contain mixtures of mono-, di- and tri-esters, plus some tetraester, the mono- and diesters are usually the predominant species in these mixtures.

Another class of suitable polyhydroxy fatty acid esters for use in the present invention comprises certain glyceryl monoesters, preferably glyceryl monoesters of $C_{16}$–$C_{22}$ saturated fatty acids such as glyceryl monostearate, glyceryl monopalmitate, and glyceryl monobehenate. Again, like the sorbitan esters, glyceryl monoester mixtures will typically contain some di- and triester. However, such mixtures should contain predominantly the glyceryl monoester species to be useful in the present invention.

Another class of suitable polyhydroxy fatty acid esters for use in the present invention comprise certain sucrose fatty acid esters, preferably the $C_{12}$–$C_{22}$ saturated fatty acid esters of sucrose. Sucrose monoesters are particularly preferred and include sucrose monostearate and sucrose monolaurate.

Suitable polyhydroxy fatty acid amides for use in the present invention will have the formula:

wherein $R^1$ is H, $C_1$–$C_4$ hydrocarbyl, 2-hydroxyethyl, 2-hydroxypropyl, methoxyethyl, methoxypropyl or a mixture thereof, preferably $C_1$–$C_4$ alkyl, methoxyethyl or methoxypropyl, more preferably $C_1$ or $C_2$ alkyl or methoxypropyl, most preferably $C_1$ alkyl (i.e., methyl) or methoxypropyl; and $R^2$ is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; and Z is a polyhydroxyhydrocarbyl moiety having a linear hydrocarbyl chain with at least 3 hydroxyls directly connected to the chain, See U.S. Pat. No. 5,174,927 (Honsa), issued Dec. 29, 1992 (herein incorporated by reference) which discloses these polyhydroxy fatty acid amides, as well as their preparation.

The Z moiety preferably will be derived from a reducing sugar in a reductive amination reaction; most preferably glycityl. Suitable reducing sugars include glucose, fructose, maltose, lactose, galactose, mannose, and xylose. High dextrose corn syrup, high fructose corn syrup, and high maltose corn syrup can be utilized, as well as the individual sugars listed above. These corn syrups can yield mixtures of sugar components for the Z moiety.

The Z moiety preferably will be selected from the group consisting of —$CH_2$-$(CHOH)_n$—$CH_2OH$, —$CH(CHOH)$-$[(CHOH)_{n-1}]$—$CH_2OH$, —$CHOH$—$CH_2$-$(CHOH)_2$ $(CHOR^3)(CHOH)$—$CH_2OH$, where n is an integer from 3 to 5, and $R^3$ is H or a cyclic or aliphatic monosaccharide. Most preferred are the glycityls where n is 4, particularly —$CH_2$-$(CHOH)_4$—$CH_2OH$.

In the above formula, $R^1$ can be, for example, N-methyl, N-ethyl, N-propyl, N-isopropyl, N-butyl, N-2-hydroxyethyl, N-methoxypropyl or N-2-hydroxypropyl, $R^2$ can be selected to provide, for example, cocamides, stearamides, oleamides, lauramides, myristamides, capricamides, palmitamides, tallowamides, etc. The Z moiety can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

The most preferred polyhydroxy fatty acid amides have the general formula:

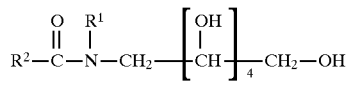

wherein $R^1$ is methyl or methoxypropyl; $R^2$ is a $C_{11}$–$C_{17}$ straight-chain alkyl or alkenyl group. These include N-lauryl-N-methyl glucamide, N-lauryl-N-methoxypropyl glucamide, N-cocoyl-N-methyl glucamide, N-cocoyl-N-methoxypropyl glucamide, N-palmityl-N-methoxypropyl glucamide, N-tallowyl-N-methyl glucamide, or N-tallowyl-N-methoxypropyl glucamide.

As previously noted, some of the immobilizing agents require an emulsifier for solubilization in the emollient. This is particularly the case for certain of the glucamides such as the N-alkyl-N-methoxypropyl glucamides having HLB values of at least about 7. Suitable emulsifiers will typically include those having HLB values below about 7. In this regard, the sorbitan esters previously described, such as the sorbitan stearates, having HLB values of about 4.9 or less have been found useful in solubilizing these glucamide immobilizing agents in petrolatum. Other suitable emulsifiers include steareth-2 (polyethylene glycol ethers of stearyl alcohol that conform to the formula $CH_3(CH_2)_{17}$ $(OCH_2CH_2)_nOH$, where n has an average value of 2), sorbitan tristearate, isosorbide laurate, and glyceryl monostearate. The emulsifier can be included in an amount sufficient to solubilize the immobilizing agent in the emollient such that a substantially homogeneous mixture is obtained. For example, an approximately 1:1 mixture of N-cocoyl-N-methyl glucamide and petrolatum that will normally not melt into a single phase mixture, will melt into a single phase mixture upon the addition of 20% of a 1:1 mixture of steareth-2 and sorbitan tristearate as the emulsifier.

The amount of immobilizing agent that should be included in the emollient composition will depend on a variety of factors, including the particular emollient involved, the particular immobilizing agent involved, whether an emulsifier is required to solubilize the immobilizing agent in the emollient, the other components in the emollient composition and like factors. The emollient composition can comprise from about 5 to about 80% of the immobilizing agent. Preferably, the emollient composition comprises from about 5 to about 50%, most preferably from about 10 to about 40%, of the immobilizing agent.

3. Optional Hydrophilic Surfactant

The interlabial device of the present invention is preferably disposed of by flushing the same down a conventional toilet. In such cases, it may be desirable that the interlabial device be sufficiently wettable so that it will not float. Depending upon the particular immobilizing agent used in the emollient composition, an additional hydrophilic surfactant (or a mixture of hydrophilic surfactants) may, or may not, be required to improve wettability. For example, some immobilizing agents, such as N-cocoyl-N-methoxypropyl glucamide have HLB values of at least about 7 and are sufficiently wettable without the addition of hydrophilic surfactant. Other immobilizing agents such as the $C_{16}$–$C_{18}$ fatty alcohols having HLB values below about 7 may require addition of hydrophilic surfactant to improve wettability. Similarly, a hydrophobic emollient such as petrolatum may require the addition of a hydrophilic surfactant.

Suitable hydrophilic surfactants are preferably miscible with the emollient and the immobilizing agent so as to form homogeneous mixtures. Because of possible skin sensitivity of those using the interlabial device, these surfactants should also be relatively mild and non-irritating to the skin. Typically, these hydrophilic surfactants are nonionic to be non-irritating to the skin.

Suitable nonionic surfactants are preferably substantially nonmigratory after the emollient composition is applied to the interlabial device and will typically have HLB values in the range of from about 4 to about 20, preferably from about 7 to about 20. To be nonmigratory, these nonionic surfactants will typically have melt temperatures greater than the temperatures commonly encountered during storage, shipping, merchandising, and use of absorbent articles, e.g., at least about 30° C. In this regard, these nonionic surfactants will preferably have melting points similar to those of the immobilizing agents previously described.

Suitable nonionic surfactants for use in emollient compositions include alkylglycosides; alkylglycoside ethers as described in U.S. Pat. No. 4,011,389 (Langdon, et al), issued Mar. 8, 1977; alkylpolyethoxylated esters such as Pegosperse 1000 MS (available from Lonza, Inc., Fair Lawn, N.J.), ethoxylated sorbitan mono-, di- and/or tri-esters of $C_{12}$–$C_{18}$ fatty acids having an average degree of ethoxylation of from about 2 to about 20, preferably from about 2 to about 10, such as TWEEN 60 (sorbitan esters of stearic acid having an average degree of ethoxylation of about 20) and TWEEN 61 (sorbitan esters of stearic acid having an average degree of ethoxylation of about 4), and the condensation products of aliphatic alcohols with from about 1 to about 54 moles of ethylene oxide. The alkyl chain of the aliphatic alcohol is typically in a straight chain (linear) configuration and contains from about 8 to about 22 carbon atoms. Particularly preferred are the condensation products of alcohols having an alkyl group containing from about 11 to about 22 carbon atoms with from about 2 to about 30 moles of ethylene oxide per mole of alcohol. Examples of such ethoxylated alcohols include the condensation products of myristyl alcohol with 7 moles of ethylene oxide per mole of alcohol, the condensation products of coconut alcohol (a mixture of fatty alcohols having alkyl chains varying in length from 10 to 14 carbon atoms) with about 6 moles of ethylene oxide. A number of suitable ethoxylated alcohols are commercially available, including TERGITOL 15-S-9 (the condensation product of $C_{11}$–$C_{15}$ linear alcohols with 9 moles of ethylene oxide), marketed by Union Carbide Corporation; KYRO EOB (condensation product of $C_{13}$–$C_{15}$ linear alcohols with 9 moles of ethylene oxide), marketed by The Procter & Gamble Co., the NEODOL brand name surfactants marketed by Shell Chemical Co., in particular NEODOL 25-12 (condensation product of $C_{12}$–$C_{15}$ linear alcohols with 12 moles of ethylene oxide) and NEODOL 23-6.5T (condensation product of $C_{12}$–$C_{13}$ linear alcohols with 6.5 moles of ethylene oxide that has been distilled (topped) to remove certain impurities), and especially the PLURAFAC brand name surfactants marketed by BASF Corp., in particular PLURAFAC A-38 (a condensation product of a $C_{18}$ straight chain alcohol with 27 moles of ethylene oxide). (Certain of the hydrophilic surfactants, in particular ethoxylated alcohols such as NEODOL 25-12, can also function as alkyl ethoxylate emollients). Other examples of preferred ethoxylated alcohol surfactants include ICI's class of Brij surfactants and mixtures thereof, with Brij 76 ( i.e., Steareth-10) and Brij 56 (i.e., Cetyl-10) being especially preferred. Also, mixtures of cetyl alcohol and stearyl alcohol ethoxylated to an average degree of ethoxylation of from about 10 to about 20 may also be used as the hydrophilic surfactant.

Another type of suitable surfactant for use in the present invention includes Aerosol OT, a dioctyl ester of sodium sulfosuccinic acid marketed by American Cyanamid Company.

Still another type of suitable surfactant for use in the present invention includes silicone copolymers such as General Electric SF 1188 (a copolymer of a polydimethylsiloxane and a polyoxyalkylene ether) and General Electric SF 1228 (a silicone polyether copolymer). These silicone surfactants can be used in combination with the other types of hydrophilic surfactants discussed above, such as the ethoxylated alcohols. These silicone surfactants have been found to be effective at concentrations as low as 0.1%, more preferably from about 0.25 to about 1.0%, by weight of the emollient composition.

The amount of hydrophilic surfactant required to increase the wettability of the emollient composition to a desired level will depend upon the HLB value and level of immobilizing agent used, the BLB value of the surfactant used and like factors. The emollient composition can comprise from about 1 to about 50% of the hydrophilic surfactant when needed to increase the wettability properties of the composition. Preferably, the emollient composition comprises from about 1 to about 25%, most preferably from about 10 to about 20%, of the hydrophilic surfactant when needed to increase wettability.

It is also possible that a surfactant can be used which is separately applied to the interlabial device, and is not included in the emollient composition. If a surfactant is separately applied to the interlabial device, it is preferably applied to the back surface 20B of the same so that it does not come in contact with the wearer's body.

In other embodiments, particularly where the interlabial device is not provided with a liquid impervious backsheet, the surfactant could be eliminated altogether. In such cases, the interlabial device will be sufficiently wettable that it is flushable. The back surface of such an interlabial device will typically not have an emollient coating thereon, and will readily wet and sink when placed in a toilet.

4. Other Optional Components

Emollient compositions can comprise other optional components typically present in emollient, creams, and emollients of this type. These optional components include water, viscosity modifiers, pH modifiers, buffers, perfumes, disinfectant antibacterial actives, pharmaceutical actives, film formers, deodorants, opacifiers, astringents, solvents, organic acids, preservatives, anti-viral actives, drugs, vitamins, aloe vera, panthenol, and the like. In addition, stabilizers can be added to enhance the shelf life of the emollient composition such as cellulose derivatives, proteins and lecithin. All of these materials are well known in the art as additives for such formulations and can be employed in appropriate amounts in the emollient compositions for use in the present invention.

C. Treating the Interlabial Structure With Emollient Composition

The body-contacting surface of the interlabial device 20 is pre-treated. The body-contacting surface 20A is treated with a substance or an emollient (such as a liquid) which is suitable for contact with the wearer's skin and which will help or aid in maintaining the hydration level of the labial tissue and reduce friction therewith.

In preparing lotioned interlabial products of the present invention, the emollient composition is applied to the body-contacting surface 20A of the interlabial product. Any of a variety of application methods that evenly distribute lubricious materials having a molten or liquid consistency can be used. Suitable methods include spraying, printing (e.g., flexographic printing), coating (e.g., gravure coating), extrusion, or combinations of these application techniques, e.g. spraying the emollient composition on a rotating surface, such as a calender roll, that then transfers the composition to the body-contacting surface of the interlabial device 20.

The manner of applying the emollient composition to the interlabial device should be such that the body-contacting surface 20A does not become saturated with the emollient composition. If the body-contacting surface 20A becomes saturated with the emollient composition, there is a greater potential for the emollient to block the pores or other openings in the body-contacting surface, reducing the ability to transmit fluid through the body-contacting surface to the absorbent portions of the interlabial device. Also, saturation of the body-contacting surface 20A is not required to obtain the benefits described herein.

The emollient composition is preferably applied to the body-contacting surface 20A of the interlabial device in an amount ranging from about 0.1 mg/cm$^2$ to about 30 mg/cm$^2$ more preferably from about 1 mg/cm$^2$ to about 15 mg/cm$^2$ (mg of emollient per square centimeters of coated body-contacting surface). Because the emollient is substantially immobilized on the surface of the body-contacting surface, less emollient composition is needed to impart the desired benefits. Such relatively low levels of emollient composition are adequate to impart the desired benefits to the interlabial device, yet do not saturate the interlabial device's absorbency and/or wettability properties.

The emollient composition may be applied to the entire body-contacting surface of the interlabial device, or portions thereof. For example, the emollient composition may be applied to the body-contacting portion of the main absorbent portion, to the body-contacting portion of the flexible extensions, or to the body-contacting portion of both the main absorbent portion and the flexible extensions. Preferably, the emollient composition is applied to the body-contacting portion of both the main absorbent portion and any flexible extensions.

The emollient composition can also be applied nonuniformly to the body-contacting surface of the interlabial device. By "nonuniform" is meant that the amount, pattern of distribution, etc. of the emollient composition can vary over the body-contacting surface. For example, some portions of the body-contacting surface can have greater or lesser amounts of emollient composition, including portions of the surface that do not have any emollient composition on it. If the emollient is applied nonuniformly, the levels of the emollient specified above are preferably averages of the amount of coating applied to the entire surface.

The emollient composition can be applied to the interlabial device at any point during assembly. For example, the emollient composition can be applied to the body-contacting surface of the finished interlabial device before it has been packaged. The emollient composition can also be applied to components of the interlabial device before they are combined with the other raw materials to form the finished interlabial device.

The emollient composition may be applied from a melt thereof to the body-contacting surface of the interlabial device. If the emollient composition melts at a temperature above ambient temperatures, it can be applied as a heated coating to the body-contacting surface. Typically, the emollient composition is heated to a temperature in the range from about 35° to about 100° C., preferably from 40° to about 90° C., prior to being applied to the body-contacting surface of the interlabial device. Once the melted emollient composition has been applied to the body-contacting surface of the interlabial device, it is allowed to cool and solidify to form solidified coating or film on the body-contacting surface. Preferably, the application process is designed to aid in the cooling/set up of the emollient.

In applying the emollient composition to interlabial devices, spraying, gravure coating and extrusion coating methods are preferred. One preferred method, when the interlabial device is provided with a topsheet, is spraying the emollient on the topsheet before the topsheet is assembled with the other raw materials into the finished product. In carrying out this method, a web of topsheet material is unwound from parent topsheet roll and advanced to a spray station where one side of the web is sprayed with a hot, molten (e.g., 65° C.) emollient composition. After leaving spray station, the web of topsheet material becomes an emollient-treated topsheet which is thereafter used in the assembly of the finished product.

An alternative preferred method involves continuous or intermittent spraying of the emollient composition on the body-contacting surface of the assembled or partially assembled interlabial device. When it is said that the emollient composition can be applied to a partially assembled interlabial device, there are a number of ways this can be accomplished. These include, but are not limited to the following. If the interlabial device is provided with flexible extensions, the web of material that is converted into the flexible extensions can be treated before the material is joined to the main absorbent portion to form the interlabial device. The main absorbent portion could similarly be treated separately before the flexible extensions are joined thereto. In this regard, it is contemplated that the main absorbent portion will initially be in the form of a continuous rope-like web that will be intermittently cut into discrete lengths to form a plurality of main absorbent portions. It will often be most convenient to treat the main absorbent portion before it is cut into discrete lengths.

In treating the interlabial device by spraying the emollient onto the assembled or partially assembled device, the interlabial device or desired portion or component thereof can be carried in any suitable manner to a spray station where the body-contacting surface of the interlabial device is sprayed with a hot, molten (e.g., 65° C.) emollient composition. After leaving the spray station, the interlabial device has an emollient coated body-contacting surface. The amount of emollient composition transferred to body-contacting surface can be controlled by: (1) the rate at which the molten emollient composition is sprayed from spray station; and/or (2) the speed at which the interlabial device travels under the spray station.

Providing the interlabial device with a coating of emollient provides a number of advantages. The emollient-treated absorbent device provides a reduction in frictional discomfort associated with rubbing of the device against the labial walls and sticking of the surfaces of the device to the labial walls. The interlabial device also has less of a drying sensation to the inside surfaces of the wearer's labia due to the presence of the emollient. In addition, as shown by comparing FIGS. 11 and 12, the interlabial device can be inserted into the space between the wearer's labia with less friction so that it will more easily be fully inserted into the desired wearing position.

Figure 11:
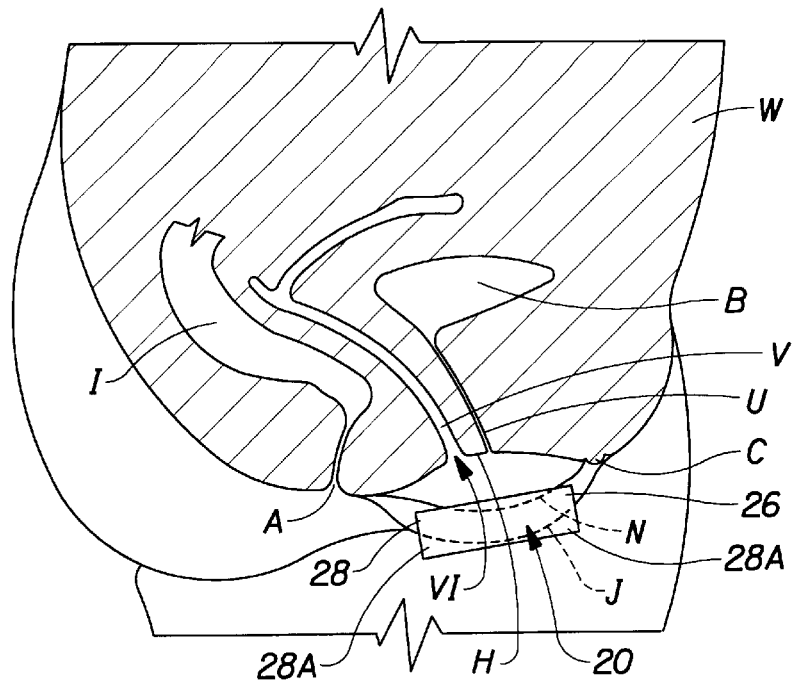
FIG. 11 is a sectional view of the wearer's body showing how a hypothetical prior art interlabial device that is not treated with an emollient may fit.

FIG. 11 shows a hypothetical example of a prior art interlabial device that is not treated with an emollient. FIG. 11 shows a prior art interlabial pad in place in a wearer's body. When the user attempts to insert such the device, the friction between the body-contacting surface of the device and the inside walls of the wearer's labia may prevent the device from being fully inserted as shown in FIG. 11. This may prevent the device from providing maximum protection against leakage. It may also result in portions of the lower portion of the device, such as lower corner portions 28A, remaining outside the labial vestibule. When the wearer sits, these lower corner portions 28A may be pressed upward causing discomfort to the wearer.

FIG. 12 shows how, on the other hand, the emollient-treated interlabial device of the present invention will tend to be capable of being more fully inserted into the labial vestibule so that the lower corner portions reside completely inside the wearer's labial vestibule.

Another advantage of the interlabial device of the present invention is that the emollients described herein are substantially free of water. Hydrous emollients are less preferred because such materials can support bacterial growth during storage of the product prior to shipment to the consumer.

In other embodiments, the emollients described herein could be applied to other types of absorbent articles, particularly other types of feminine hygiene articles, such as sanitary napkins, panty liners, incontinence devices, and tampons. The relatively lower molecular weight and melting temperature of the emollients described herein make them particularly suitable for use with absorbent articles that have an apertured film topsheet such as those topsheet materials described above. Without wishing to be bound to any particular theory this is believed to be so because such topsheets will not have fibers which help maintain the coating thereon by the emollient embedding into the spaces between the same. Higher molecular weight and higher melting point temperature materials will typically readily flake off apertured films, when such films are flexed.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

TEST METHODS

Absorbent Capacity

Absorbent capacity may be determined as follows. The test is performed on samples that have been conditioned by leaving them in a room at 50% relative humidity and at 73° F. for a period of two hours prior to the test. The test should be performed under similar conditions.

The article is weighed to the nearest 0.1 gram. The article is then submerged in a beaker of sterile 0.9% saline solution (obtainable from the Baxter Travenol Company of Deerfield, Ill.), such that the article is totally submerged and is not bent or otherwise twisted or folded. The article is submerged for 10 minutes. The article is removed from the saline and laid horizontally on a wire mesh screen having square openings 0.25 inches by 0.25 inches (0.64 cm by 0.64 cm) for five minutes to allow the saline to drain out to the article. Both sides of the article are then covered with absorbent blotters, such as the filter paper #631 available from the Filtration Science Corp., Eaton-Dikeman Division of Mount Holly Springs, Pa. A uniform 17.6 grams per square centimeter load is placed over the article to squeeze excess fluid out. The absorbent blotters are replaced every 30 seconds until the amount of fluid transferred to the absorbent blotters is less than 0.5 grams in a 30 second period. Next, the article is weighed to the nearest 0.1 gram and the dry weight of the article is subtracted. The difference in grams is the absorbent capacity of the article.

Three Point Bend Test

The Three Point Bend Test is performed on samples that have been conditioned by leaving them in a room at 50% relative humidity and at 73° F. for a period of two hours prior to the test. The test should be performed under similar conditions.

Figure 13:
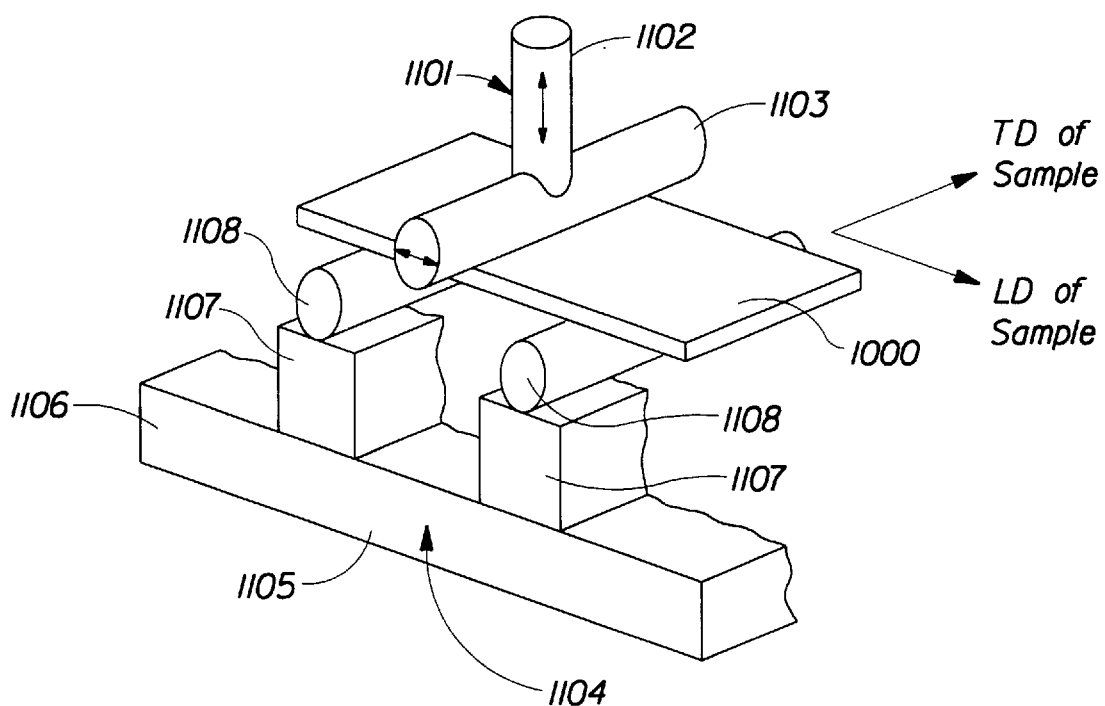
FIG. 13 is a schematic perspective view of the Three Point Bend Test apparatus.

The three point bend test uses an INSTRON Model 4502 tensile and compression testing machine, which is available from Instron Corporation of Canton, Mass. The test also uses a special displacement "T-rod" and a special test sample holder. As shown in FIG. 13, the "T-rod" 1101 comprises a pair of 6.40 mm to diameter metal rods perpendicularly mounted together. The drive rod 1102 is about 125 mm long and the push rod 1103 is about 75 mm long. Preferably, the end of the drive rod 1102 is tapered to fit the circumference of the push rod 1103 and the two are glued, welded and/or screwed to each other. The opposite end of the drive rod 1102 is mounted to the crosshead unit of the INSTRON machine. The test sample holder 1104 comprises a fixture base 1105 for positioning and supporting a pair of supporting rods 1108. The fixture base 1105 comprises a base 1105 and two rectangular supports 1107 mounted in parallel on the base 1106. The base 1106 and the supports 1107 are each preferably made of LEXAN (plexiglas) plate of about 10 mm to about 13 mm thickness. A supporting rod 1108 of the same materials as the "T-bar" and about 150 mm long is mounted on each support 1107 of the fixture base 1105. The supporting rods 1108 are mounted so as to leave 10 mm of open space between them (measured at the point on each rod which is closest to the other). As shown in FIG. 11, the "T-rod" 1101 is centered between the supporting rods 1108.

The INSTRON machine is set for a crosshead speed of 2.0 in/min (50.8 mm/min). The INSTRON machine is set up so that the crosshead unit will travel 10 mm down and back for each sample tested.

Prior to testing of a sample, the T-rod 1101 is lowered until it is resting directly on top on one of the supporting rods 1108. The vertical position of the T-rod 1101 is "zeroed" when the load as it rests on supporting rod 1108 is about 1 gram$_f$. The T-rod 1101 is then raised 5 mm from this zero position and centered between both supporting rods 1108.

The sample 1000 to be tested can be a piece of material taken from one of the flexible extensions. The sample 1000 taken from the flexible extensions should have a dimension of about 25 mm in the longitudinal direction LD and a dimension in the transverse direction of about 10 mm. If the flexible extensions on the product to be tested are too small, a larger sample of the same material should be used for the test. The sample is placed so that the push rod 1103 is running parallel to a side of the sample that was oriented in the transverse direction TD.

The T-rod 1101 is then allowed to travel through a complete 10 mm cycle (i.e., 10 mm down and 10 mm back up). Consequently, the T-rod 1101 will make contact with the sample 1000 after about 5 mm and bend the sample about an additional 5 mm. The bending resistance is the peak force required to bend the sample as the T-rod travels through a complete 10 mm cycle.

Burst Strength Test

Overview

A test specimen, held between annular clamps, is subjected to increasing force that is applied by a 0.625 inch diameter, polished stainless steel ball. The burst strength is that force that causes the sample to fail. Burst strength may be measured on wet or dry samples.

Apparatus

| | |
|---|---|
| Burst Tester | Intelect-II-STD Tensile Test Instrument, Cat. No. 1451-24PGB or the Thwing-Albert Burst Tester are both suitable. Both instruments are available from Thwing-Albert Instrument Co., Philadelphia, PA. The instruments must be equipped with a 2000 g load cell and, if wet burst measurements are to be made, the instruments must be equipped with a load cell shield and a front panel water shield. |
| Conditioned Room | Temperature and humidity should be controlled to remain within the following limits: Temperature: 73 ± 3° F. (23° C. ± 2° C.) Humidity: 50 ± 2% Relative Humidity |
| Paper Cutter | Scissors or other equivalent may be used |

| | |
|---|---|
| Pan | For soaking wet burst samples, suitable to sample size |
| Solution | Water for soaking wet burst samples should be equilibrated to the temperature of the conditioned room. |
| Timer | Appropriate for measuring soak time |

Sample preparation

1) Cut the sample to a size appropriate for testing (minimum sample size 4.5 in×4.5 in). If the sample to be tested is too small (e.g., a flexible extension with overall dimensions less than 4.5 in×4.5 in) a larger sample of the same material should be used to determine wet burst strength. Prepare a minimum of five samples for each condition to be tested.

2) If wet burst measurements are to be made, place an appropriate number of cut samples into a pan filled with temperature-equilibrated water.

Equipment Setup

1) Set the burst tester up according to the manufacturer's instructions. If an Intelect-II-STD Tensile Test Instrument is to be used the following are appropriate:

Speed: 12.7 centimeters per minute

Break Sensitivity: 20 grams

Peak Load: 2000 grams

2) Calibrate the load cell according to the expected burst strength.

Measurement and Reporting

1) Operate the burst tester according to the manufacturer's instructions to obtain a burst strength measurement for each sample.

2) Record the burst strength for each sample and calculate an average and a standard deviation for the burst strength for each condition.

3) Report the average and standard deviation for each condition to the nearest gram.

Report the average and the standard deviation for each group of four samples.

This concludes the test.

Water Dispersion Test

Apparatus

| | |
|---|---|
| Stirrer | Magnetic, Thermolyne type Model S7225 or 7200 (no substitutions). Permanently inscribe a circle 3.5 inches (8.9 centimeter) on the top surface of the stirrer. The center of the circle must be coincident with the geometric center of the stirrer. |
| Stirring Bar | 2.5 inch (6.2 centimeter) TEFLON coated with spinning ring. Permanently mark one end of the bar with black ink for a distance of 0.5 inch (1.2 centimeter) back from the tip. |
| Thermometer | 30 to 120° F. with 1 degree divisions |
| Timer | Digital stopwatch |
| Stroboscope | Variable speed stroboscope, model 964 available from Strobette, Power Instrument, Inc. of Skokie, IL is suitable |
| Beaker | Kimax brand 2000 milliliter with spout (no substitution), Inscribe a fill mark at a height of 5.6 inches (14.3 centimeters) from the flat bottom of the beaker. Do not use any beaker not having a flat bottom. |
| Conditioned Room | Temperature and humidity should be controlled to remain within the following limits: Temperature: 73 ± 3° F. (23° C. ± 2° C.) Humidity: 50 ± 2% Relative Humidity |

Test Setup

1. Fill the beaker to the fill mark with 73±3° F. tap water.
2. Place the beaker on the magnetic stirrer centering it in the inscribed circle.
3. Add the stirring bar to the beaker.
4. Turn the stroboscope on and set the speed to 1000 rpm according to the manufacturer's directions.
5. Turn the magnetic stirrer on with the on/off switch. Adjust the speed of the magnetic stirrer until the stirring bar appears to be stationary and both ends appear to be black. This indicates that the magnetic stirrer is turning at 500 rpm (i.e. half the setting on the stroboscope). Turn the magnetic stirrer off with the on/off switch.

Procedure

1. Hold a sample (e.g. an absorbent interiabial device 20) 3 to 4 inches (7.6 to 10.2 centimeters) above the surface of the water. Gently drop the sample onto the water surface, starting the timer when the sample touches the water surface.
2. Wait 5 seconds.
3. Start the magnetic stirrer with the on/off switch.
4. Record the time required until the sample separates into at least two pieces. If the motion of the stirring bar is disrupted by the sample so it no longer rotates, turn off the magnetic stirrer. Recenter the magnet without removing the sample and restart the stirrer immediately. The time recorded is the total time that the sample remains in the water, including the time required to restart the stirrer.
5. Repeat steps 1 through 4 with an additional 3 samples.

Calculation and Reporting

Calculate and report the mean and standard deviation of the water dispersibility time for the four samples tested. However, if at least one of the four samples seperates into at least two fragments during the time specified in the appended claims, the sample will be considered to be water dispersible. The term "fragments", as used herein, is not intended to include the seperation of merely a few loose fibers (that is, fibers which constitute less than 5% of the total product mass), from the sample. The interlabial devices described herein preferably disperse into at least two fragments within about 1 hour, more preferably within about 30 minutes.

This concludes the test.

Flushability

Overview

As noted above, the terms "flushable or flushability" refer to a product's capacity to pass through typical commercially available household toilets and plumbing drainage systems without causing clogging or similar problems that can be directly associated with the physical characteristics of the product. For the purpose of the appended claims, catamenial products are evaluated for flushability via relative ease of toilet bowl and trap evacuation and subsequent transport through a simulated plumbing system. The flushability of such a device should be measured by the following test procedure.

The test procedure is designed to simulate two days of normal toilet usage for a family of 4 (2 men, 2 women). The test employs a flushing sequence to simulate the following conditions: male urination visits, female urination visits (including post urinary drying with tissue), disposal of catamenial product (that is, the interlabial device or other device to be tested) with cleaning using tissue, and bowel movement visits. The amount of tissue to be used for each tissue flush is a normal loading of 2 strips of seven sheets. The normal loading is based on consumer research regarding typical habits and practices. The test is designed to simulate the conditions a product will encounter if it is flushed through a conventional toilet and into a municipal sewer or into a septic tank. Samples are evaluated for: 1) toilet bowl and trap clearance, 2) drain line blockage, and 3) disintegration during flushing.

Apparatus

Figure 14:
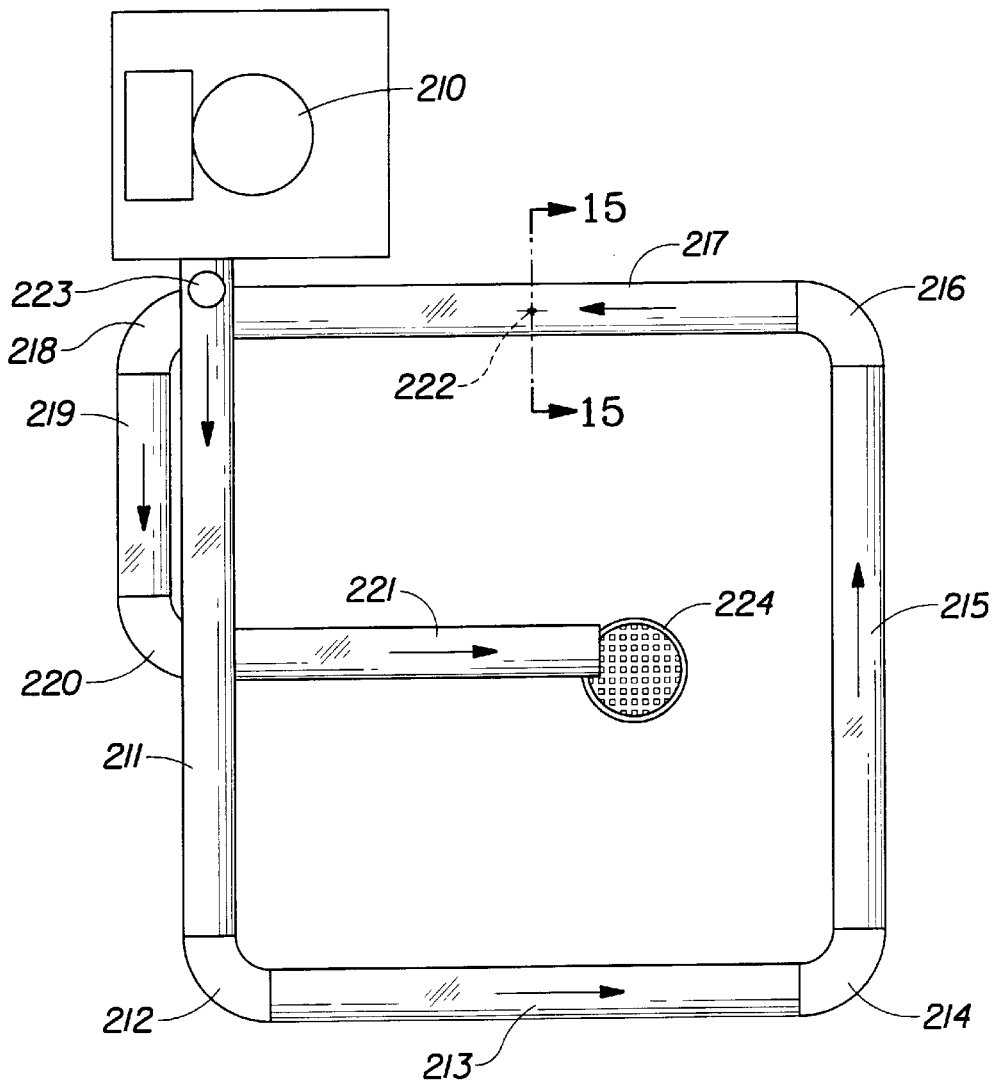
FIG. 14 is a plan view of an apparatus suitable for flushability determination according to the method described in the TEST METHODS section below.
Figure 15:
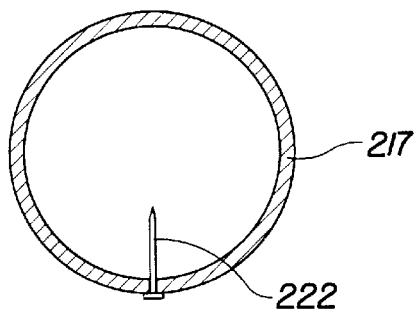
FIG. 15 is a cross-section of the flushability apparatus of FIG. 14 taken along line 15—15 thereof.

An apparatus suitable for the flushability test is shown in plan view in FIG. 14. The apparatus includes:
- a 3.5 gallon (13.2 liter) water saver siphon vortex toilet referred to as 210 (additional toilets can also be attached to the piping layout shown in FIG. 14 to evaluate the behavior of test samples using different flushing mechanisms such as commercial, pressure toilets);
- approximately 59 feet (18 meters) of 4 inch (10 cm) inside diameter acrylic pipe (as can be seen from FIG. 14, the piping is assembled in roughly a square configuration having linear runs 211, 213, 215, 217, 219, 221 approximately 10 feet (3 meters) long);
- a cast iron tee 223 slightly downstream of the toilet 210 that is open to the atmosphere for venting;
- five cast iron ninety degree elbows 212, 214, 216, 218, and 220;
- a snag 222 positioned vertically (FIG. 15) approximately 15 feet from the pipe's terminal end and approximately 1 inch (2.5 cm) long; and
- a screen (No. 4 Tyler sieve) to capture solid effluent for evaluation of disintegration.

The apparatus used for this method is set up to be equivalent to ANSI Standard A112.19.2M-1990 for Vitreous China fixtures. The piping is plumbed to provide a drop of 0.25 inch per foot (2 centimeters/meter) of pipe length.

Materials

Tissue Product used in Test: Standard CHARMIN® toilet tissue manufactured by the Procter & Gamble Company, Cincinnati, Ohio Synthetic Fecal Material Prepared according to the method described below Test Flushing Sequence The test flushing sequence simulates 2 days of normal toilet usage for a family of 4 (2 men, 2 women; based on consumer habits and practices research). The sequence of 34 total flushes consists of 14 flushes with an empty bowl, 8 flushes with tissue only, 6 flushes with tissue and a catamenial product and 6 flushes with tissue and simulated fecal matter (SFM). When it is used, the SFM is placed in the bowl just prior to the addition of tissue. The SFM loading of 160 g±5 g consists of two 1 inch (2.5 centimeter)×4 inch (10 centimeter) pieces and one 1inch (2.5 centimeter)×2 inch (5 centimeter) piece. Folded tissue strips (or the catamenial product) are placed in the bowl at 10 second intervals. Ten seconds after the final strip or catamenial product is placed into the bowl, the toilet is flushed. The flushing sequence is described below as a series of two routines combined in the following order:

Routine #1

(To be performed first 6 times for a total of 30 flushes)
1) Flush With Tissue Only—Take a drain line blockage reading 2 minutes after the water reaches the simulated obstruction, wait 1 additional minute, and move to step 2.
2) Flush With Empty Bowl. Take a drain line blockage reading 2 minutes after the water reaches the snag point and move to step 3.
3) Flush With Tissue and Catamenial Product—Take a drain line blockage reading 2 minutes after the water reaches the snag point, wait 1 additional minute, and move to step 4.
4) Flush With Empty Bowl. Take a drain line blockage reading 2 minutes after the water reaches the snag point and move to step 5.
5) Flush With Tissue and Simulated Fecal Matter (SFM). Take a drain line blockage reading 2 minutes after the water reaches the snag point, wait 1 additional minute.

Routine #2

(To be performed 1 time)
1) Flush With Tissue Only—Take a drain line blockage reading 2 minutes after the water reaches the snag point, wait 1 additional minute, and move to step 2.
2) Flush With Empty Bowl. Take a drain line blockage reading 2 minutes after the water reaches the snag point and move to step 3.
3) Flush With Tissue Only—Take a drain line blockage reading 2 minutes after the water reaches the snag point, wait 1 additional minute, and move to step 4.
4) Flush With Empty Bowl. Take a drain line blockage reading 2 minutes after the water reaches the snag point.

Total number of flushes per sequence is 34.

If, after the second flush in the flushing sequence, the product remains in the bowl or trap after flushing, the tissue and or catamenial product is plunged into the drainage line manually and the flushing sequence will continue. After completion of each trial loading, the drainage pipe will be cleared prior to beginning subsequent testing.

The above described flushing sequence is repeated three times for each test product.

Data Reporting

The degree of drain line blockage is determined by measuring the length of water dammed up behind the obstruction. Graduations are marked every 12 inches (30 centimeters) on the drainpipe upstream of the obstruction. Each one foot length that the water is backed up corresponds to 0.25 inch (0.6 centimeter) or 6.25% of blockage at the obstruction point. Test product residues which exit the drainpipe are also collected.

The following data are recorded for each evaluation:

1) Incidence of failure (%) of catamenial product to clear bowl and trap in one flush
2) Incidence of failure (%) of catamenial product to clear bowl and trap in two flushes
3) Incidence of product on simulated snag
4) Maximum level (%) of drain line blockage
5) Cumulative level (%) of drain line blockage over 2 days.

Preferably, the products described herein will completely clear the bowl at least 70% of the time in two or fewer flushes, more preferably at least 80% of the time in one flush, and most preferably at least about 95% of the time in one flush. The products described herein will preferably have a maximum level of drain line blockage of less than or equal to about 80%. The products described herein will preferably have a cumulative level of drain line blockage over 2 days of less than or equal to about 50%.

Preparation of Synthetic Fecal Material

I. Materials Needed:

Feclone synthetic fecal matter (900 grams);
(Available from Siliclone Studio, Valley Forge, Pa. as product BFPS7 dry concentrate)
Tap water at 100° C. (6066 grams)

II. Equipment Needed:

Mixer (Available from Hobart Corp., Troy, Ohio as Model A200)
Extruder (Available from Hobart Corp., Troy, Ohio as Model 4812)
Disposable Centrifuge tubes with screw caps (50 ml) (Available from VWR Scientific, Chicago, Ill. as Catalog No. 21-008-176)
Water Bath to control temperature to 37° C.

III. Preparation:

1. Pour the 100° C. water into the mixing bowl of the mixer and add the dry Feclone concentrate.
2. Mix on low for 1 minute.
3. Mix on medium speed for 2 minutes.
4. After the material is well mixed, transfer to the extruder.
5. Using an ice pick, punch a small hole in the tip of each centrifuge tube.
6. Extrude the Feclone into the centrifuge tubes.
7. Cap the centrifuge tubes and store in the refrigerator.
8. Before using, put the tubes in the water bath at 38° C.

SPECIFIC ILLUSTRATIONS OF THE PREPARATION OF EMOLLIENT-TREATED INTERLABIAL DEVICES

The following are specific illustrations of interlabial devices with emollient compositions in accordance with the present invention:

EXAMPLE 1

A. Preparation of Emollient Compositions

A water free emollient composition (Emollient A) is made by mixing the following melted (i.e., liquid) components together: Mineral Oil (Carnation White Mineral Oil, USP made by Witco Corp.), Cetearyl Alcohol (a mixed linear $C_{16}$–$C_{18}$ primary alcohol made by the Procter & Gamble Company under the name TA-1618); Steareth-2 (Brij 72, a $C_{18}$ linear alcohol ethoxylate having an average degree of ethoxylation of 2, made by ICI America), and General Electric SF1550 (a phenyl trimethicone made by the General Electric Company). The weight percentages of these components are shown in Table I below:

TABLE I

| Component | Weight % |
| --- | --- |
| Mineral Oil | 50 |
| Cetearyl Alcohol | 35 |
| Steareth-2 | 14 |
| Phenyl Trimethicone | 01 |

B. Preparation of Emollient-Treated Interlabial Device by Hot Melt Spraying

Emollient Composition A is placed into a heated tank operating at a temperature of 125° F. The composition is subsequently sprayed (using a Dynatec E84B1759 spray head, operating at a temperature of 165° F. and an atomization pressure of 2.40 psig) onto the body-contacting surface of the interlabial device. Add-on level=2.3 mg/cm².

EXAMPLE 2

A. Preparation of Emollient Compositions

A water free emollient composition (Emollient B) is made by mixing the following melted (i.e., liquid) components together: Mineral Oil (Carnation White Mineral Oil, USP made by Witco Corp.), Cetearyl Alcohol (a mixed linear $C_{16}$–$C_{18}$ primary alcohol made by the Procter & Gamble Company under the name TA-1618), and General Electric SF1632 (a cetearyl methicone made by the General Electric Company). The weight percentages of these components are shown in Table II below:

TABLE II

| Component | Weight % |
| --- | --- |
| Mineral Oil | 65 |
| Cetearyl Alcohol | 34 |
| Cetearyl Methicone | 01 |

B. Preparation of Emollient-Treated Interlabial Device by Hot Melt Spraying

Emollient Composition B is placed into a heated tank operating at a temperature of 125° F. The composition is subsequently sprayed (using a Dynatec E84B1758 spray head, operating at a temperature of 165° F. and an atomization pressure of 2.40 psig) body-contacting surface of the interlabial device. Add-on level=0.006 g/in² (2.3 mg/cm²).

EXAMPLE 3

A. Preparation of Emollient Composition

A water free emollient composition (Emollient C) is made by mixing the following melted (i.e., liquid) components together: White Protopet® IS (white petrolatum made by Witco Corp.), Cetearyl Alcohol (a mixed linear $C_{16}$–$C_{18}$ primary alcohol made by the Procter & Gamble Company under the name TA-1618); Cetearth 10 (a blend or mixture of $C_{16}$ and $C_{18}$ alcohols ethoxylated to an average of 10 ethoxylate units obtained from BASF Corp. of Mount Olive, N.J.), and General Electric SF1632 (a cetearyl methicone made by the General Electric Company). The weight percentages of these components are shown in Table I below:

A water free emollient composition (Emollient C) is made by mixing together the following melted (i.e., liquid) components in the weight percentages shown in the Table III below according to the procedure of Example 2:

TABLE III

| Component | Weight % |
|---|---|
| WhiteProtopet ® IS | 50 |
| Cetearyl Alcohol | 35 |
| Cetearth-10 | 14 |
| Cetearyl Methicone | 01 |

B. Preparation of Emollient-Treated Interlabial Device by Hot Melt Spraying

Emollient Composition C is placed into a heated tank operating at a temperature of 125° F. The composition is subsequently sprayed (using a Dynatec E84B1758 spray head, operating at a temperature of 165° F. and an atomization pressure of 2.40 psig) body-contacting surface of the interlabial device. Add-on level=0.004 g/in² (1.5 mg/cm²).

EXAMPLE 4

A. Preparation of Emollient Composition

A water free emollient composition (Emollient D) is made by mixing the following melted (i.e., liquid) components together: White Protopet® IS (white petrolatum made by Witco Corp.); Dow Corning 556 Cosmetic Grade Fluid(a polyphenylmethylsiloxane made by the Dow Corning Corporation), An example of a particularly preferred paraffin wax is Parrafin S.P. 434 (a paraffin wax made by Strahl and Pitsch Inc.); Cetearyl Alcohol (a mixed linear $C_{16}$–$C_{18}$ primary alcohol made by the Procter & Gamble Company under the name TA-1618); PEG 2000 (a polyethylene glycol having a MW of 2000 made by Sigma-Aldrich Corp). The weight percentages of these components are shown in Table IV below:

TABLE IV

| Component | Weight % |
|---|---|
| WhiteProtopet ® IS | 52 |
| Polyphenylmethyl-siloxane | 10 |
| Paraffin Wax | 15 |
| Cetearyl Alcohol | 20 |
| PEG 2000 | 3 |

B. Preparation of Emollient-Treated Interlabial Device by Hot Melt Spraying

Emollient Composition D is placed into a heated tank operating at a temperature of 150° F. The composition is subsequently sprayed (using a Dynatec E84B1758 spray head, operating at a temperature of 170° F. and an atomization pressure of 2.40 psig) body-contacting surface of the intertabial device. Add-on level=0.006 g/in² (2.3 mg/cm²).

While particular embodiments of the present invention have been illustrated and described, it would be obvious to those skilled in the art that various other changes and modifications can be made without departing from the spirit and scope of the invention.

What is claimed is:

1. An absorbent interlabial device insertable into the interlabial space of a female wearer said interlabial device having a body-contacting surface at least a portion of which is capable of maintaining contact with the inside surfaces of the wearer's labia when the device is worn, said interlabial device comprising:

a main absorbent portion comprising an upper portion comprising part of said body-contacting surface and a lower portion, said upper portion facing toward the vestibule floor of said wearer during insertion into said interlabial space and leading said lower portion during insertion therein, said lower portion being opposed to said upper portion and upon insertion of said absorbent device into said interlabial space said lower portion facing away from the floor of the vestibule of said wearer; and a pair of flexible extensions joined to said upper portion of said main absorbent portion and extending downwardly and outwardly therefrom, said flexible extensions comprising part of said body-contacting surface, wherein at least a portion of said body-contacting surface comprises an effective amount of an emollient composition which is semi-solid or solid at 20° C. and which is partially transferable to the wearer's skin, said emollient composition comprising a substantially water free polysiloxane emollient having a plastic or liquid consistency at 20° C.

2. The absorbent device of claim 1 wherein said portion of said body-contacting surface that comprises said emollient composition is said upper portion of said main absorbent portion.

3. The absorbent device of claim 1 wherein said portion of said body-contacting surface that comprises said flexible extensions is said upper portion of said main absorbent portion.

4. The absorbent device of claim 1 wherein both said upper portion of said main absorbent portion and said flexible extensions comprise said emollient composition.

5. An absorbent interlabial device for wearing in the interlabial space of a female wearer said interlabial device having a body-contacting surface at least a portion of which is capable of maintaining contact with the inside surfaces of the wearer's labia when said device is worn, and an absorbent portion, wherein at least a portion of said body-contacting surface comprises an effective amount of a polysiloxane emollient composition, said emollient composition comprising a substantially water free polysiloxane emollient having a plastic or fluid consistency at 20° C.

6. The absorbent device of claim 2 wherein said emollient composition comprises:

(i) from about 5 to about 95% of a substantially water free polysiloxane emollient having a plastic or fluid consistency at 20° C.; and (ii) from about 5 to about 90% of an agent capable of immobilizing said emollient on said body-contacting surface, said immobilizing agent having a melting point of at least about 35° C.

7. The absorbent device of claim 6 wherein said polsiloxane emollient contains about 5% or less water and comprises a polysiloxane compound having a viscosity at 37° C. of from about 5 to about 2,000 centistokes.

8. The absorbent device of claim 7 wherein said polysiloxane compound is a polymethylsiloxane compound.

9. The absorbent device of claim 8 wherein said polysiloxane compound is a polymethylsiloxane compound substituted with a functional group selected from the group consisting of phenyl, amino, alkyl, carboxyl, hydroxyl, ether, polyether, aldehyde, ketone, amide, ester, thiol groups, and mixtures thereof.

10. The absorbent device of claim 9 wherein said substituted polymethylsiloxane compound is a polyphenylmethylsiloxane compound.

11. The absorbent device of claim 6 wherein said emollient composition further comprises a petroleum based emollient selected from the group consisting of mineral oil, petrolatum, and mixtures thereof.

12. The absorbent device of claim 11 wherein said petroleum based emollient is petrolatum.

13. The absorbent device of claim 11 wherein said petroleum based emollient is mineral oil.

14. The absorbent device of claim 6 wherein said immobilizing agent is selected from the group consisting of polyhydroxy fatty acid esters, polyhydroxy fatty acid amides, $C_{14}$–$C_{22}$ fatty alcohols, $C_{12}$–$C_{22}$ fatty acids, $C_{12}$–$C_{22}$ fatty alcohol ethoxylates, waxes, and mixtures thereof.

15. The absorbent device of claim 6 wherein said emollient composition comprises from about 5 to about 50% of said immobilizing agent, said immobilizing agent having a melting point of at least about 40° C.

16. The absorbent device of claim 15 wherein said immobilizing agent comprises a $C_{14}$–$C_{22}$ fatty alcohol.

17. The absorbent device of claim 16 wherein said immobilizing agent comprises a $C_{16}$–$C_{18}$ fatty alcohol selected from the group consisting of cetyl alcohol, stearyl alcohol, and mixtures thereof.

18. The absorbent device of claim 6 wherein said immobilizing agent comprises a paraffin or microcrystalline wax.

19. The absorbent device of claim 6 wherein said emollient composition further comprises from about 1 to about 50% of a hydrophilic surfactant, said hydrophilic surfactant having an HLB value of at least about 4.

20. The absorbent device of claim 19 wherein said emollient composition further comprises from about 1 to about 25% of said hydrophilic surfactant, said hydrophilic surfactant being nonionic and having an HLB value of from about 4 to about 20.

21. The absorbent device of claim 20 wherein said hydrophilic surfactant comprises an ethoxylated alcohol having an alkyl chain of from about 8 to about 22 carbon atoms and having an average degree of ethoxylation ranging from about 1 to about 54.

22. The absorbent device of claim 21 wherein said ethoxylated alcohol has an alkyl chain of from about 11 to about 22 carbon atoms and having an average degree of ethoxylation ranging from about 2 to about 30.

23. The absorbent device of claim 5 wherein the quantity of emollient composition on said body contacting portion of said absorbent device ranges from about 0.1 mg/cm² to about 30 mg/cm².

24. The absorbent device of Claim 23 wherein the quantity of emollient composition on said body contacting portion of said absorbent device ranges from about 1 mg/cm² to 15 mg/cm².

25. The absorbent device of claim 5 wherein said emollient composition further comprises from about 1 to about 50% of a hydrophilic surfactant, said hydrophilic surfactant having an HLB value of at least about 4.

26. An absorbent interlabial device according to claim 5 that is sufficiently flushable that it completely clears the bowl under the Flushability Test at least about 70% of the time in two or fewer flushes.

27. An absorbent interlabial device according to claim 5 that is sufficiently flushable that it completely clears the bowl under the Flushability Test at least about 95% of the time in one flush.

28. An absorbent interlabial device according to claim 5 which disperses into at least two fragments as measured by the Water Dispersion Test in less than or equal to about one hour.

29. An absorbent interlabial device according to claim 5 wherein said emollient coating comprises a multi-component emollient composition having at least one component with a peak heat absorption of less than 37° C.

30. An absorbent interlabial device which fits at least partially within a female wearer's labial vestibule, said interlabial device having a body-contacting surface, wherein at least a portion of said absorbent device is capable of maintaining contact with the inside surfaces of the wearer's labia when said device is worn, and an absorbent portion, wherein at least a portion of said body-contacting surface comprises an effective amount of a emollient composition which is semi-solid or solid at 20° C., said emollient composition comprising a substantially water free poysiloxane emollient having a plastic or liquid consistency at 20° C. wherein said absorbent interlabial device has a capacity of greater than or equal to about 2.5 grams of saline when said device is measured under 0.25 psi of pressure.

31. The absorbent device of claim 30 having a capacity greater than or equal to about 4.0 grams of saline.

32. The absorbent device of claim 31 further comprising a non-ionic surfactant thereon.

* * * * *

UNITED STATES PATENT AND TRADEMARK OFFICE
CERTIFICATE OF CORRECTION

PATENT NO.   : 5,891,126
DATED        : April 6, 1999
INVENTOR(S)  : Thomas Ward Osborn, III et al.

It is certified that error appears in the above-identified patent and that said Letters Patent is hereby corrected as shown below:

Column 3, line 5, delete "lo".

Column 5, line 56, after "device" insert -- 20 --.

Column 12, line 50, "Dec.30," should read -- Dec. 30, --.

Column 16, line 13, "surfactant(s)," should read -- surfactant(s); --.

Column 20, line 7, after "about" insert -- 10 --.

Column 25, line 58, "BLB" should read -- HLB --.

Column 27, line 8, "thereof" should read -- thereof. --.

Column 29, line 62, delete "to".

Column 32, line 28, "interiabial" should read -- interlabial --.

Column 37, line 67, "intertabial" should read -- interlabial --.

Signed and Sealed this

Seventh Day of March, 2000

Attest:

Attesting Officer

Q. TODD DICKINSON

Commissioner of Patents and Trademarks